United States Patent
Bedoukian et al.

(10) Patent No.: US 10,278,389 B2
(45) Date of Patent: May 7, 2019

(54) FORMULATIONS FOR CONTROL AND REPELLENCY OF BITING ARTHROPODS

(71) Applicant: BEDOUKIAN RESEARCH, INC., Danbury, CT (US)

(72) Inventors: Robert H. Bedoukian, West Redding, CT (US); Patrick Murray Foley, New Haven, CT (US)

(73) Assignee: Bedoukian Research, Inc., Danbury, CT (US)

(*) Notice: Subject to any disclaimer, the term of this patent is extended or adjusted under 35 U.S.C. 154(b) by 0 days.

(21) Appl. No.: 15/699,554

(22) Filed: Sep. 8, 2017

(65) Prior Publication Data

US 2018/0064107 A1    Mar. 8, 2018

Related U.S. Application Data

(60) Provisional application No. 62/451,436, filed on Jan. 27, 2017, provisional application No. 62/384,939, filed on Sep. 8, 2016.

(51) Int. Cl.
*A61K 31/201* (2006.01)
*A01N 31/06* (2006.01)

(52) U.S. Cl.
CPC .................... *A01N 31/06* (2013.01)

(58) Field of Classification Search
CPC .................................... A61K 31/201
USPC ......................................... 514/690
See application file for complete search history.

(56) References Cited

U.S. PATENT DOCUMENTS

| | | | |
|---|---|---|---|
| 2005/0187289 A1* | 8/2005 | Dolan | A01N 27/00 514/457 |
| 2015/0133406 A1* | 5/2015 | Bedoukian | A01N 31/02 514/159 |
| 2016/0165899 A1* | 6/2016 | Bissinger | A61K 8/31 424/745 |
| 2018/0213774 A1* | 8/2018 | Bedoukian | A01N 35/06 |

* cited by examiner

*Primary Examiner* — Raymond J Henley, III
(74) *Attorney, Agent, or Firm* — Ohlandt, Greeley, Ruggiero & Perle, L.L.P.

(57) ABSTRACT

This disclosure relates to a method for the control or repellency of biting arthropods. The method comprises bringing the biting arthropods into contact with a biting arthropod repellent formulation. The biting arthropod repellent formulation comprises an alkoxy nootkatol separate from, or in combination, or in synergistic combination, with skin or plant derived compounds and compounds structurally similar to them (e.g., ketones, cyclic ketones, esters, gamma or delta lactones, and branched and/or unsaturated carboxylic acids), and/or one or more repellents selected from the group consisting of DEET®, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds. This disclosure also relates to a biting arthropod repellent formulation comprising an alkoxy nootkatol separate from, or in combination, or in synergistic combination, with the skin or plant derived compounds and compounds structurally similar to them, and/or the one or more repellents.

20 Claims, No Drawings

FORMULATIONS FOR CONTROL AND REPELLENCY OF BITING ARTHROPODS

RELATED APPLICATIONS

This application claims the benefit of U.S. Patent Application Ser. No. 62/451,436, filed Jan. 27, 2017, and U.S. Patent Application Ser. No. 62/384,939, filed Sep. 8, 2016, both of which are incorporated herein by reference in their entirety. This application is related to copending U.S. patent application Ser. No. 15/699,563, filed Sep. 8, 2017, which claims the benefit of U.S. Patent Application Ser. No. 62/451,437, filed Jan. 27, 2017, and U.S. Patent Application Ser. No. 62/384,939, filed Sep. 8, 2016.

BACKGROUND OF THE DISCLOSURE

1. Field of the Disclosure

This disclosure relates to repellent formulations of compounds used as agents to control and repel biting arthropods, and especially ticks, mosquitoes and bed bugs. Also, this disclosure relates to repellent formulations of compounds used synergistically as agents to control and repel biting arthropods, and especially ticks, mosquitoes and bed bugs.

2. Description of the Related Art

Many mammals, including humans, have suffered the action of mosquitoes and other biting insects. The blood sucking of mosquitoes results in an itching sensation and often a rash. Also, many mosquitoes cause potentially life-threatening illness. *Aedes aegypti* can transmit dengue fever, yellow fever and Zika virus, *Anopheles quadrimaculatus* can transmit malaria and *Culex quinquefasciatus* can transmit West Nile disease. One possible solution to these problems is applying an insect repelling agent to the skin as a topical repellent. Applying arthropod or insect repellents to fabric, like mosquito netting, is another way of reducing arthropod, insect or mosquito bites.

DEET®, namely N,N-Diethyl-3-methylbenzamide, is widely used against biting arthropods and insects, but is characterized by an unseemly bad smell, is not particularly long lasting in its effect and it dissolves plastics. Moreover, several safety questions have been raised concerning the use of DEET® and some governments have restricted the amount of the active component that may be employed in formulations. This itself presents a further problem since the efficacy of DEET® declines over time and therefore it needs to be formulated at higher than effective dosages in order to maintain its effectiveness. Furthermore, some insects and pests have developed resistance to DEET® due to its wide spread usage. Other repellents, such as para-menthane-3,8-diol (PMD), are relatively expensive.

As such, there is a need to provide a biting insect repellent formulation that can reduce or eliminate the use of standard repellents like DEET®, PMD or sec-butyl-2-(2-hydroxyethyl) piperidine carboxylate ("Picaridin"). Additionally, there is a need to provide an insect or pest repellent formulation which is non-toxic to the people, plants, and other animals which may be exposed to areas of application. A further need is for a pest or insect control formulation that comprises long lasting effects, thereby limiting the need for frequent re-application to treated areas. A further need is for such a pest or insect control formulation that may be toxic to certain pests or insects but not to humans and that do not produce an undesirable effect on the environment.

SUMMARY OF THE DISCLOSURE

In accordance with this disclosure, control and repellency of biting arthropods, and particularly ticks, mosquitoes and bed bugs, is obtained by contact of the biting arthropods with biting arthropod repellent formulations based on an alkoxy nootkatol acting separate from, or in combination, or in synergistic combination, with skin or plant derived compounds and compounds structurally similar to them, and/or in combination with conventional repellents such as DEET®, PMD, Picaridin, IR3535, or other nitrogen-containing repellent compounds such as amides, amines and nitrogen-containing heterocyclic compounds.

This disclosure also relates in part to a method for the control or repellency of biting arthropods. The method comprises bringing the biting arthropods into contact with a biting arthropod repellent formulation. The biting arthropod repellent formulation comprises an alkoxy nootkatol.

This disclosure further relates in part to a method for the control or repellency of biting arthropods. The method comprises bringing the biting arthropods into contact with a biting arthropod repellent formulation. The biting arthropod repellent formulation comprises:

(I) any combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range;

(2) compounds of the structure (A)

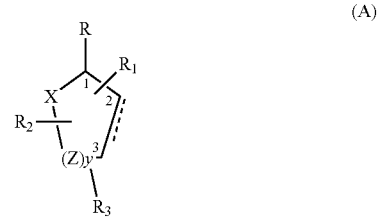

wherein:
R is selected from —OH, =O, —OC(O)R$_4$, —OR$_6$, and —(OR$_6$)$_2$, wherein each R$_6$ is independently selected from an alkyl group containing from about 1 to about 4 carbon atoms and R$_4$ is a branched or straight chain, saturated or unsaturated, hydrocarbyl group with zero to two double bonds and from about 1 to about 15 carbon atoms;
X is O or CH$_2$, with the proviso that when X is O, R, can only be =O;
each Z is independently selected from (CH) and (CH$_2$);
y is a numeral selected from 1 and 2;
R$_1$ is selected from H or a branched or straight chain, saturated or unsaturated, hydrocarbyl group with zero to two double bonds and from about 1 to about 15 carbon atoms;
R$_2$ is selected from H and a branched or straight chain, saturated or unsaturated, hydrocarbyl group with zero to three double bonds and from about 1 to about 15 carbon atoms;
R$_3$ is selected from H, a branched or straight chain, saturated or unsaturated, hydrocarbyl group with zero to three double bonds and from about 1 to about 15 carbon atoms, —$(CH_2)_nOH$, —$C(O)OR_5$, —$CH_2C(O)OR_7$, —$CH_2C(O)R_8$, —$C(O)NR_9R_{10}$, and —$CH_2C(O)NR_{11}R_{12}$, wherein each of $R_8$, $R_7$, $R_8$, $R_9$, $R_{10}$, $R_{11}$ and $R_{12}$ is independently selected from H and a branched or straight chain, saturated or unsaturated, hydrocarbyl group with zero to three double bonds and from about 1 to about 15 carbon atoms, and n is n integer of from 1 to 12;

the bond between the 2 and 3 positions in the ring structure may be a single or a double bond; and wherein the compounds of structure (A) contain from about 1 to about 20 carbon atoms except where R is =O, X=$CH_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof; and (4) esters of branched or unbranched, straight chain or cyclic, saturated or unsaturated, carboxylic acids containing from about 3 to about 18 carbon atoms or any range of carbon atoms within said range, including isomers thereof; or (II) any combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds.

This disclosure yet further relates in part to a method for the control or repellency of biting arthropods. The method comprises bringing the biting arthropods into contact with a synergistic biting arthropod repellent formulation. The synergistic biting arthropod repellent formulation comprises:

(I) any synergistic combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range;

(2) compounds of the structure (A)

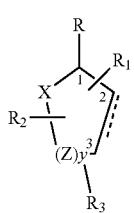

(A)

wherein:
R is selected from —OH, =O, —$OC(O)R_4$, —$OR_6$, and —$(OR_6)_2$, wherein each $R_6$ is independently selected from an alkyl group containing from about 1 to about 4 carbon atoms and $R_4$ is a branched or straight chain, saturated or unsaturated, hydrocarbyl group with zero to two double bonds and from about 1 to about 15 carbon atoms;
X is O or $CH_2$, with the proviso that when X is O, R, can only be =O;
each Z is independently selected from (CH) and ($CH_2$);
y is a numeral selected from 1 and 2;

$R_1$ is selected from H or a branched or straight chain, saturated or unsaturated, hydrocarbyl group with zero to two double bonds and from about 1 to about 15 carbon atoms;

$R_2$ is selected from H and a branched or straight chain, saturated or unsaturated, hydrocarbyl group with zero to three double bonds and from about 1 to about 15 carbon atoms;

$R_3$ is selected from H, a branched or straight chain, saturated or unsaturated, hydrocarbyl group with zero to three double bonds and from about 1 to about 15 carbon atoms, —$(CH_2)_nOH$, —$C(O)OR_5$, —$CH_2C(O)OR_7$, —$CH_2C(O)R_8$, —$C(O)NR_9R_{10}$, and —$CH_2C(O)NR_{11}R_{12}$, wherein each of $R_5$, $R_7$, $R_8$, $R_9$, $R_{10}$, $R_{11}$ and $R_{12}$ is independently selected from H and a branched or straight chain, saturated or unsaturated, hydrocarbyl group with zero to three double bonds and from about 1 to about 15 carbon atoms, and n is n integer of from 1 to 12;

the bond between the 2 and 3 positions in the ring structure may be a single or a double bond; and wherein the compounds of structure (A) contain from about 11 to about 20 carbon atoms except where R is =O, X=$CH_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof; and (4) esters of branched or unbranched, straight chain or cyclic, saturated or unsaturated, carboxylic acids containing from about 3 to about 18 carbon atoms or any range of carbon atoms within said range, including isomers thereof; or (II) any synergistic combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds. The synergistic combination of the alkoxy nootkatol in combination with the one or more of compounds (a) and/or the synergistic combination of the alkoxy nootkatol in combination with the one or more repellents, produces a combined effect greater than the sum of their separate effects.

This disclosure also relates in part to a biting arthropod repellent formulation comprising an alkoxy nootkatol.

This disclosure further relates in part to a biting arthropod repellent formulation comprising:

(I) any combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range;

(2) compounds of the structure (A)

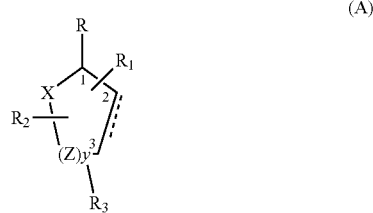

wherein:
R is selected from —OH, =O, —OC(O)R$_4$, —OR$_6$, and —(OR$_6$)$_2$, wherein each R is independently selected from an alkyl group containing from about 1 to about 4 carbon atoms and R$_4$ is a branched or straight chain, saturated or unsaturated, hydrocarbyl group with zero to two double bonds and from about 1 to about 15 carbon atoms;
X is O or CH$_2$, with the proviso that when X is O, R, can only be =O;
each Z is independently selected from (CH) and (CH$_2$):
y is a numeral selected from 1 and 2:
R$_1$ is selected from H or a branched or straight chain, saturated or unsaturated, hydrocarbyl group with zero to two double bonds and from about 1 to about 15 carbon atoms;
R$_2$ is selected from H and a branched or straight chain, saturated or unsaturated, hydrocarbyl group with zero to three double bonds and from about 1 to about 15 carbon atoms:
R$_3$ is selected from H, a branched or straight chain, saturated or unsaturated, hydrocarbyl group with zero to three double bonds and from about 1 to about 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, and —CH$_2$C(O)NR$_{11}$R$_{12}$, wherein each of R$_5$, R$_7$, R$_8$, R$_9$, R$_{10}$, R$_{11}$ and R$_{12}$ is independently selected from H and a branched or straight chain, saturated or unsaturated, hydrocarbyl group with zero to three double bonds and from about 1 to about 15 carbon atoms, and n is n integer of from 1 to 12; the bond between the 2 and 3 positions in the ring structure may be a single or a double bond; and
wherein the compounds of structure (A) contain from about 11 to about 20 carbon atoms except where R is =O, X=CH$_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof; and (4) esters of branched or unbranched, straight chain or cyclic, saturated or unsaturated, carboxylic acids containing from about 3 to about 18 carbon atoms or any range of carbon atoms within said range, including isomers thereof; or (II) any combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl) amino]propanoate (IR3535), and other nitrogen-containing repellents including amines, amides, and nitrogen-containing heterocyclic compounds.

This disclosure yet further relates in part to a synergistic biting arthropod repellent formulation comprising:

(I) any synergistic combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range;

(2) compounds of the structure (A)

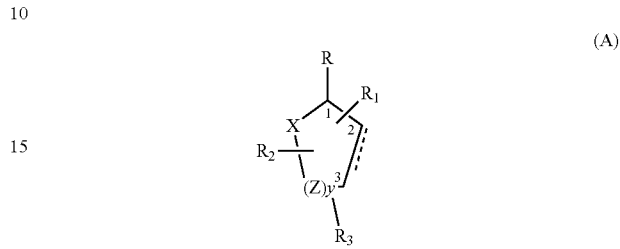

wherein:
R is selected from —OH, =O, —OC(O)R$_4$, —OR$_6$, and —(OR$_6$)$_2$, wherein each R$_6$ is independently selected from an alkyl group containing from about 1 to about 4 carbon atoms and R$_4$ is a branched or straight chain, saturated or unsaturated, hydrocarbyl group with zero to two double bonds and from about 1 to about 15 carbon atoms;
X is O or CH$_2$, with the proviso that when X is O, R, can only be =O;
each Z is independently selected from (CH) and (CH$_2$);
y is a numeral selected from 1 and 2;
R$_1$ is selected from H or a branched or straight chain, saturated or unsaturated, hydrocarbyl group with zero to two double bonds and from about 1 to about 15 carbon atoms;
R$_2$ is selected from H and a branched or straight chain, saturated or unsaturated, hydrocarbyl group with zero to three double bonds and from about 1 to about 15 carbon atoms;
R$_3$ is selected from H, a branched or straight chain, saturated or unsaturated, hydrocarbyl group with zero to three double bonds and from about 1 to about 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, and —CH$_2$C(O)NR$_{11}$R$_{12}$, wherein each of R$_5$, R$_7$, R$_8$, R$_9$, R$_{10}$, R$_{11}$ and R$_{12}$ is independently selected from H and a branched or straight chain, saturated or unsaturated, hydrocarbyl group with zero to three double bonds and from about 1 to about 15 carbon atoms, and n is n integer of from 1 to 12;
the bond between the 2 and 3 positions in the ring structure may be a single or a double bond; and
wherein the compounds of structure (A) contain from about 1 to about 20 carbon atoms except where R is =O, X=CH$_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof, and (4) esters of branched or unbranched, straight chain or cyclic, saturated or unsaturated, carboxylic acids containing from about 3 to about 18 carbon atoms or any range of carbon atoms within said range, including isomers thereof, or (II) any synergistic combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds. The synergistic combination of the alkoxy nootkatol in combination with the one or more of compounds (a) and/or the synergistic combination of the alkoxy nootkatol in combination with the one or more repellents, produces a combined effect greater than the sum of their separate effects.

Further objects, features and advantages of the present disclosure will be understood by reference to the following drawings and detailed description.

DESCRIPTION OF THE PREFERRED EMBODIMENTS

As used herein, the term "synergistic" refers to any combination of compounds and/or repellents that produces a combined effect greater than, preferably significantly greater than, the sum of their separate effects. In the formulations of this disclosure, the combined effect is greater repellency or protection time.

As used herein, the term "alkoxy nootkatol" refers to any alkoxy nootkatols that exhibit control and/or repellency of biting arthropods, acting separate from, or in combination, or in synergistic combination, with one or more of compounds (a) as described herein, and/or one or more repellents selected from the group consisting of N,N-Diethyl-3-methylbenzamide, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds. Illustrative alkoxy groups include, for example, C1-C12 alkoxy groups. A preferred alkoxy nootkatol of this disclosure is methoxy nootkatol.

Control and repellency of biting arthropods, and especially ticks, mosquitoes and bed bugs, is obtained by contact of the biting arthropods with biting arthropod repellent formulations based on an alkoxy nootkatol acting separate from, or in combination, or in synergistic combination, with biting arthropod repellents found on human/animal skin or in plants taken from the certain chemical families (such as, for example ketones, cyclic ketones, esters, gamma or delta lactones and branched and/or unsaturated carboxylic acids similar to those found on human/animal skin or in plants), and/or an alkoxy nootkatol acting separate from, or in combination, or in synergistic combination, with conventional repellents like DEET®, PMD, Picaridin, IR3535, or nitrogen-containing repellent compounds such as amides, amines and nitrogen-containing heterocyclic compounds, such as pyrazines.

In an embodiment, a method is provided for the control or repellency of biting arthropods. The method comprises bringing the biting arthropods into contact with a biting arthropod repellent formulation. The biting arthropod repellent formulation comprises an alkoxy nootkatol.

In another embodiment, a biting arthropod repellent formulation is provided that comprises an alkoxy nootkatol.

The alkoxy nootkatol is preferably present in an amount from about 0.5 weight percent to about 30 weight percent, based on the total weight of the biting arthropod repellent formulation.

A preferred biting arthropod repellent formulation comprises methoxy nootkatol represented by the formula

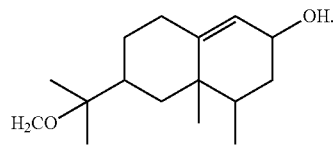

In yet another embodiment, a method is provided for the control or repellency of biting arthropods. The method comprises bringing the biting arthropods into contact with a biting arthropod repellent formulation. The biting arthropod repellent formulation comprises:

(I) any combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range:

(2) compounds of the structure (A)

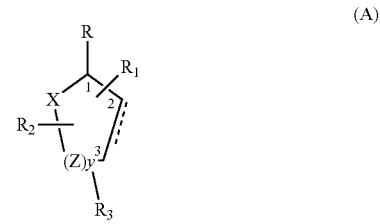

(A)

wherein:
R is selected from —OH, =O, —OC(O)R$_4$, —OR$_6$, and —(OR$_6$)$_2$, wherein each R$_6$ is independently selected from an alkyl group containing from about 1 to about 4 carbon atoms and R$_4$ is a branched or straight chain, saturated or unsaturated, hydrocarbyl group with zero to two double bonds and from about 1 to about 15 carbon atoms;
X is O or CH$_2$, with the proviso that when X is O, R, can only be =O; each Z is independently selected from (CH) and (CH$_2$);
y is a numeral selected from 1 and 2;
R$_1$ is selected from H or a branched or straight chain, saturated or unsaturated, hydrocarbyl group with zero to two double bonds and from about 1 to about 15 carbon atoms;
R$_2$ is selected from H and a branched or straight chain, saturated or unsaturated, hydrocarbyl group with zero to three double bonds and from about 1 to about 15 carbon atoms;
R$_3$ is selected from H, a branched or straight chain, saturated or unsaturated, hydrocarbyl group with zero to three double bonds and from about 1 to about 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, and —CH$_2$C(O)NR$_{11}$R$_{12}$, wherein each of R$_5$, R$_7$, R$_8$, R$_9$, R$_{10}$, R$_{11}$ and R$_{12}$ is independently selected from H and a branched or straight chain, saturated or unsaturated, hydrocarbyl group with zero to three double bonds and from about 1 to about 15 carbon atoms, and n is n integer of from 1 to 12;
the bond between the 2 and 3 positions in the ring structure may be a single or a double bond; and
wherein the compounds of structure (A) contain from about 1 to about 20 carbon atoms except where R is =O, X=CH$_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof; and (4) esters of branched or unbranched, straight chain or cyclic, saturated or unsaturated, carboxylic acids containing from about 3 to about 18 carbon atoms or any range of carbon atoms within said range, including isomers thereof; or (II) any combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl) amino]propanoate (IR3535), and other nitrogen-containing repellents including amines, amides, and nitrogen-containing heterocyclic compounds.

The alkoxy nootkatol is preferably present in an amount from about 0.5 weight percent to about 30 weight percent, and the one or more compounds (a) and/or the one or more repellents selected from the group consisting of DEET®, para-menthane-3,8-diol (PMD), Picaridin, ethyl 3-[acetyl (butyl)amino]propanoate (IR3535), and other nitrogen-containing repellents including amines, amides, and nitrogen-containing heterocyclic compounds are preferably present in an amount from about 0.5 weight percent to about 25 weight percent, based on the total weight of the biting arthropod repellent formulation.

In still another embodiment, a biting arthropod repellent formulation is provided that comprises an alkoxy nootkatol, and one or more of the compounds (a) and/or one or more of the repellents selected from the group consisting of DEET®, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds.

In another embodiment, a method is provided for the control or repellency of biting arthropods. The method comprises bringing the biting arthropods into contact with a synergistic biting arthropod repellent formulation. The synergistic biting arthropod repellent formulation comprises:

(I) any synergistic combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range;

(2) compounds of the structure (A)

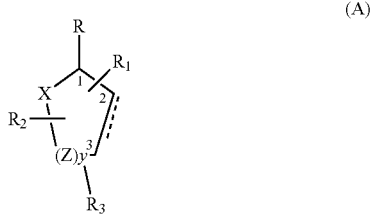

(A)

wherein:
R is selected from —OH, =O, —OC(O)R$_4$, —OR$_6$, and —(OR$_6$)$_2$, wherein each R$_6$ is independently selected from an alkyl group containing from about 1 to about 4 carbon atoms and R$_4$ is a branched or straight chain, saturated or unsaturated, hydrocarbyl group with zero to two double bonds and from about 1 to about 15 carbon atoms;

X is O or CH$_2$, with the proviso that when X is O, R, can only be =O;

each Z is independently selected from (CH) and (CH$_2$);

y is a numeral selected from 1 and 2;

R$_1$ is selected from H or a branched or straight chain, saturated or unsaturated, hydrocarbyl group with zero to two double bonds and from about 1 to about 15 carbon atoms;

R$_2$ is selected from H and a branched or straight chain, saturated or unsaturated, hydrocarbyl group with zero to three double bonds and from about 1 to about 15 carbon atoms;

R$_3$ is selected from H, a branched or straight chain, saturated or unsaturated, hydrocarbyl group with zero to three double bonds and from about 1 to about 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, and —CH$_2$C(O)NR$_{11}$R$_{12}$, wherein each of R$_5$, R$_7$, R$_8$, R$_9$, R$_{10}$, R$_{11}$ and R$_{12}$ is independently selected from H and a branched or straight chain, saturated or unsaturated, hydrocarbyl group with zero to three double bonds and from about 1 to about 15 carbon atoms, and n is an integer of from 1 to 12;

the bond between the 2 and 3 positions in the ring structure may be a single or a double bond; and wherein the compounds of structure (A) contain from about 11 to about 20 carbon atoms except where R is =O, X=CH$_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof; and (4) esters of branched or unbranched, straight chain or cyclic, saturated or unsaturated, carboxylic acids containing from about 3 to about 18 carbon atoms or any range of carbon atoms within said range, including isomers thereof, or (II) any synergistic combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl) amino]propanoate (IR3535), and other nitrogen-containing repellents including amines, amides, and nitrogen-containing heterocyclic compounds;

wherein the synergistic combination of the alkoxy nootkatol in combination with the one or more of compounds (a) and/or the synergistic combination of the alkoxy nootkatol in combination with the one or more repellents, produces a combined effect greater than the sum of their separate effects.

The alkoxy nootkatol is present in a synergistic amount from about 0.5 weight percent to about 30 weight percent, and the one or more compounds (a) and/or the one or more repellents selected from the group consisting of DEET®, para-menthane-3,8-diol (PMD), Picaridin, ethyl 3-[acetyl (butyl)amino]propanoate (IR3535), and other nitrogen-containing repellents including amines, amides, and nitrogen-containing heterocyclic compounds are present in a synergistic amount from about 0.5 weight percent to about 25 weight percent, based on the total weight of the synergistic biting arthropod repellent formulation.

In yet another embodiment, a synergistic biting arthropod repellent formulation is provided that comprises an alkoxy nootkatol, and one or more of the compounds (a) and/or one or more of the repellents selected from the group consisting of DEET®, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds.

In still another embodiment, a synergistic biting arthropod repellent formulation is provided that comprises an alkoxy nootkatol, and two or more of the compounds (a), and/or two or more of the repellents selected from the group consisting of DEET®), para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds.

In a synergistic formulation of this disclosure, the amount of compound (a) and alkoxy nootkatol in an effective dose required to repel about 100% of a biting arthropod is less than the amount of compound (a) alone in an effective dose required to repel about 100% of the biting arthropod. Preferably, in this synergistic formulation, compound (a) can be present in an amount from about 0.5 to about 25% by weight, and alkoxy nootkatol can be present in an amount from about 0.5 to about 30% by weight, and in a weight ratio of compound (a) to alkoxy nootkatol from about 0.1:2 to about 2:0.1. More preferably, in this synergistic formulation, compound (a) can be present in an amount from about 2.5 to about 20% by weight, and alkoxy nootkatol can be present in an amount from about 2.5 to about 25% by weight, and in a weight ratio of compound (a) to alkoxy nootkatol from about 0.2:1 to about 1:0.2. Even more preferably, in this synergistic formulation, compound (a) can be present in an amount from about 5 to about 15% by weight, and alkoxy nootkatol can be present in an amount from about 5 to about 20% by weight, and in a weight ratio of compound (a) to alkoxy nootkatol from about 0.3:1 to about 1:0.3.

In a synergistic formulation of this disclosure, the amount of N,N-Diethyl-3-methylbenzamide and alkoxy nootkatol in an effective dose required to repel about 100% of a biting arthropod is less than the amount of N,N-Diethyl-3-methylbenzamide alone in an effective dose required to repel about 100% of the biting arthropod. Preferably, in this synergistic formulation, N,N-Diethyl-3-methylbenzamide can be present in an amount from about 0.5 to about 25% by weight, and alkoxy nootkatol can be present in an amount from about 0.5 to about 30% by weight, and in a weight ratio of N,N-Diethyl-3-methylbenzamide to alkoxy nootkatol from about 0.1:2 to about 2:0.1. More preferably, in this synergistic formulation, N,N-Diethyl-3-methylbenzamide can be present in an amount from about 2.5 to about 20% by weight, and alkoxy nootkatol can be present in an amount from about 2.5 to about 25% by weight, and in a weight ratio of N,N-Diethyl-3-methylbenzamide to alkoxy nootkatol from about 0.2:1 to about 1:0.2. Even more preferably, in this synergistic formulation. N,N-Diethyl-3-methylbenzamide can be present in an amount from about 5 to about 15% by weight, and alkoxy nootkatol can be present in an amount from about 5 to about 20% by weight, and in a weight ratio of N,N-Diethyl-3-methylbenzamide to alkoxy nootkatol from about 0.3:1 to about 1:0.3.

In another synergistic formulation of this disclosure, the amount of PMD and alkoxy nootkatol in an effective dose required to repel about 100% of a biting arthropod is less than the amount of PMD alone in an effective dose required to repel about 100% of the biting arthropod. Preferably, in this synergistic formulation, PMD can be present in an amount from about 0.5 to about 25% by weight, and alkoxy nootkatol can be present in an amount from about 0.5 to about 30% by weight, and in a weight ratio of PMD to alkoxy nootkatol from about 0.1:2 to about 2:0.1. More preferably, in this synergistic formulation. PMD can be present in an amount from about 2.5 to about 20% by weight, and alkoxy nootkatol can be present in an amount from about 2.5 to about 25% by weight, and in a weight ratio of PMD to alkoxy nootkatol from about 0.2:1 to about 1:0.2. Even more preferably, in this synergistic formulation. PMD can be present in an amount from about 5 to about 15% by weight, and alkoxy nootkatol can be present in an amount from about 5 to about 20% by weight, and in a weight ratio of PMD to alkoxy nootkatol from about 0.3:1 to about 1:0.3.

In yet another synergistic formulation of this disclosure, the amount of Picaridin and alkoxy nootkatol in an effective dose required to repel about 100% of a biting arthropod is less than the amount of Picaridin alone in an effective dose required to repel about 100% of the biting arthropod. Preferably, in this synergistic formulation, Picaridin can be present in an amount from about 0.5 to about 25% by weight, and alkoxy nootkatol can be present in an amount from about 0.5 to about 30% by weight, and in a weight ratio of Picaridin to alkoxy nootkatol from about 0.1:2 to about 2:0.1. More preferably, in this synergistic formulation, Picaridin can be present in an amount from about 2.5 to about 20% by weight, and alkoxy nootkatol can be present in an amount from about 2.5 to about 25% by weight, and in a weight ratio of Picaridin to alkoxy nootkatol from about 0.2:1 to about 1:0.2. Even more preferably, in this synergistic formulation, Picaridin can be present in an amount from about 5 to about 15% by weight, and alkoxy nootkatol can be present in an amount from about 5 to about 20% by weight, and in a weight ratio of Picaridin to alkoxy nootkatol from about 0.3:1 to about 1:0.3.

In another synergistic formulation of this disclosure, the amount of IR3535 and alkoxy nootkatol in an effective dose required to repel about 100% of a biting arthropod is less than the amount of IR3535 alone in an effective dose required to repel about 100% of the biting arthropod. Preferably, in this synergistic formulation, IR3535 can be present in an amount from about 0.5 to about 25% by weight, and alkoxy nootkatol can be present in an amount from about 0.5 to about 30% by weight, and in a weight ratio of IR3535 to alkoxy nootkatol from about 0.1:2 to about 2:0.1. More preferably, in this synergistic formulation, IR3535 can be present in an amount from about 2.5 to about 20% by weight, and alkoxy nootkatol can be present in an amount from about 2.5 to about 25% by weight, and in a weight ratio of IR3535 to alkoxy nootkatol from about 0.2:1 to about 1:0.2. Even more preferably, in this synergistic formulation, IR3535 can be present in an amount from about 5 to about 15% by weight, and alkoxy nootkatol can be present in an amount from about 5 to about 20% by weight, and in a weight ratio of IR3535 to alkoxy nootkatol from about 0.3:1 to about 1:0.3.

In another synergistic formulation of this disclosure, the amount of a nitrogen-containing repellent selected from an amine, amide and nitrogen-containing heterocyclic compound, and alkoxy nootkatol in an effective dose required to repel about 100% of a biting arthropod is less than the amount of nitrogen-containing repellent alone in an effective dose required to repel about 100% of the biting arthropod. Preferably, in this synergistic formulation, the nitrogen-containing repellent can be present in an amount from about 0.5 to about 25% by weight, and alkoxy nootkatol can be present in an amount from about 0.5 to about 30% by weight, and in a weight ratio of nitrogen-containing repellent to alkoxy nootkatol from about 0.1:2 to about 2:0.1. More preferably, in this synergistic formulation, the nitrogen-containing repellent can be present in an amount from about 2.5 to about 20% by weight, and alkoxy nootkatol can be present in an amount from about 2.5 to about 25% by weight, and in a weight ratio of nitrogen-containing repellent to alkoxy nootkatol from about 0.2:1 to about 1:0.2. Even more preferably, in this synergistic formulation, the nitrogen-containing repellent can be present in an amount from about 5 to about 15% by weight, and alkoxy nootkatol can be present in an amount from about 5 to about 20% by weight, and in a weight ratio of nitrogen-containing repellent to alkoxy nootkatol from about 0.3:1 to about 1:0.3.

In accordance with this disclosure, illustrative alkyl and cyclic ketones of compounds (a) include, for example, geranyl acetone (6,10-dimethyl-5,9-undecadien-2-one), farnesyl acetone (5,9,13-pentadecatrien-2-one, 6,10,14-trimethyl-) methyl undecyl ketone (2-tridecanone), methyl decyl ketone (2-dodecanone), alpha-ionone (4-(2,6,6-trimethyl-2-cyclohexenyl)-3-buten-2-one), beta ionone (4-(2,6,6-trimethyl-1-cyclohexenyl)-3-buten-2-one), alpha-isomethylionone (3-methyl-4-(2,6,6-trimethyl-2-cyclohexen-1-yl)-3-buten-2-one), isobutylionone ((E)-5-methyl-1-(2,6,6-trimethyl-1-cyclohex-2-enyl) hex-1-en-3-one), isolongifolen-9-one ((1R)-2,2,7,7-tetramethyltricyclo[6.2.1.01,6]undec-5-en-4-one), dimethylionone ((E)-2-methyl-1-(2,2,6-trimethyl-1-cyclohex-3-enyl)pent-1-en-3-one), isolongifolanone (2,2,7,7-tetramethyltricyclo[6.2.1.01,6]undecan-5-one), pseudoionone (6,10-dimethyl-3,5,9-undecatrien-2-one), 2-cyclopentylcyclopentanone, methyl nonyl ketone (2-undecanone), and 3-decen-2-one. Especially preferred are methyl decyl ketone, methyl undecyl ketone, methyl nonyl ketone, geranyl acetone, farnesyl acetone, ionone, and isolongifolenone.

Representative examples of alkyl ketones of compounds (a) include, but are not limited to, geranyl acetone having the formula

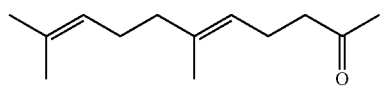

and a methyl ketone with variable chain length (e.g., R is a hydrocarbon group having from about 1 to about 18 carbon atoms) having the formula

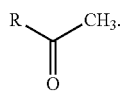

Representative preferred examples of alkyl ketones of compounds (a) include, but are not limited to, geranyl acetone, farnesyl acetone, methyl undecyl ketone, and methyl nonyl ketone.

Representative examples of compounds of structure (A) of compounds (a) include, but are not limited to, the following:

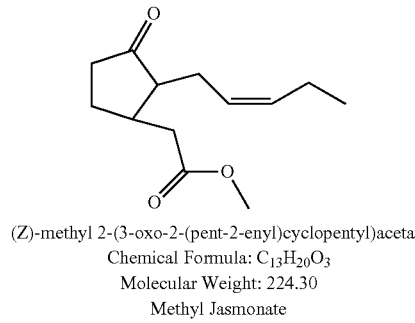

(Z)-methyl 2-(3-oxo-2-(pent-2-enyl)cyclopentyl)acetate
Chemical Formula: $C_{13}H_{20}O_3$
Molecular Weight: 224.30
Methyl Jasmonate

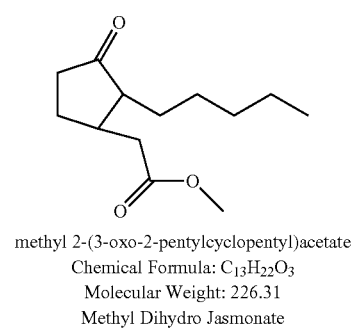

methyl 2-(3-oxo-2-pentylcyclopentyl)acetate
Chemical Formula: $C_{13}H_{22}O_3$
Molecular Weight: 226.31
Methyl Dihydro Jasmonate

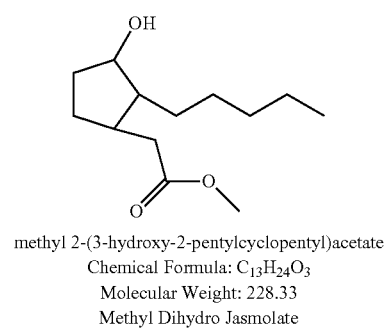

methyl 2-(3-hydroxy-2-pentylcyclopentyl)acetate
Chemical Formula: $C_{13}H_{24}O_3$
Molecular Weight: 228.33
Methyl Dihydro Jasmolate

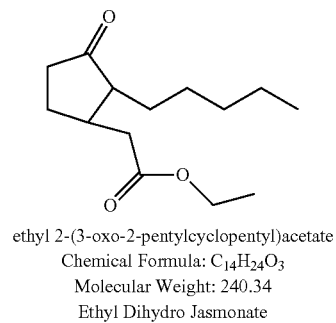

ethyl 2-(3-oxo-2-pentylcyclopentyl)acetate
Chemical Formula: $C_{14}H_{24}O_3$
Molecular Weight: 240.34
Ethyl Dihydro Jasmonate

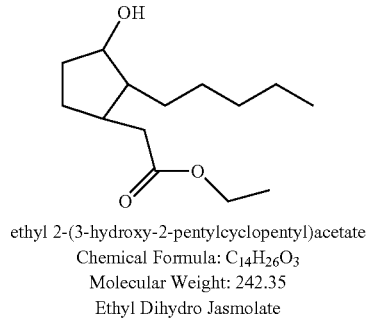

ethyl 2-(3-hydroxy-2-pentylcyclopentyl)acetate
Chemical Formula: $C_{14}H_{26}O_3$
Molecular Weight: 242.35
Ethyl Dihydro Jasmolate -continued

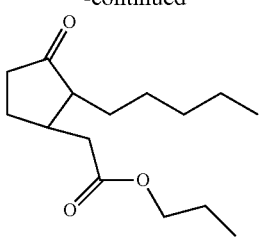

propyl 2-(3-oxo-2-pentylcyclopentyl)acetate
Chemical Formula: $C_{15}H_{26}O_3$
Molecular Weight: 254.37
Propyl Dihydro Jasmonate

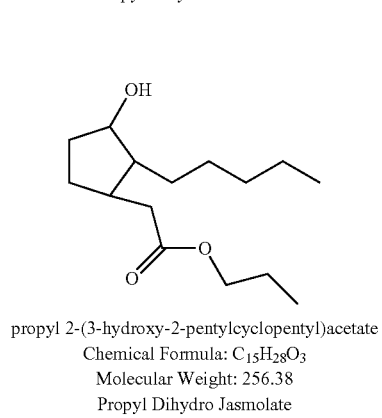

propyl 2-(3-hydroxy-2-pentylcyclopentyl)acetate
Chemical Formula: $C_{15}H_{28}O_3$
Molecular Weight: 256.38
Propyl Dihydro Jasmolate

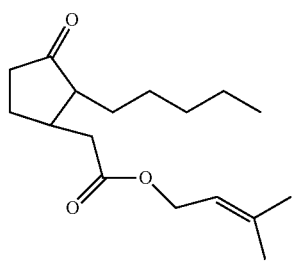

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate

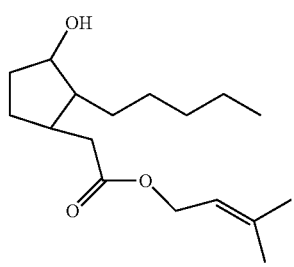

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate -continued

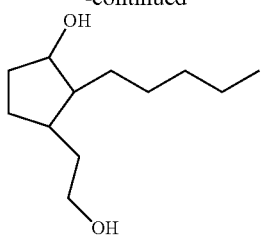

3-(2-hydroxyethyl)-2-pentylcyclopentanol
Chemical Formula: $C_{12}H_{24}O_2$
Molecular Weight: 200.32
MethylDihydroJasmodiol

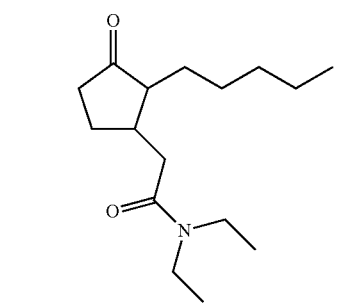

N,N-diethyl-2-(3-oxo-2-pentylcyclopentyl)acetamide
Chemical Formula: $C_{16}H_{29}NO_2$
Molecular Weight: 267.41
MDJ Amide

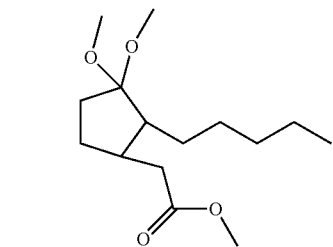

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

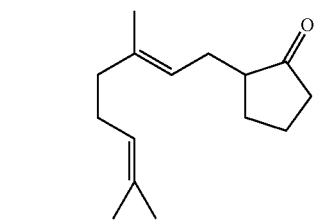

(E)-2-(3,7-dimethylocta-2,6-dienyl)cyclopentanone
Chemical Formula: $C_{15}H_{24}O$
Molecular Weight: 220.35
Apritone -continued

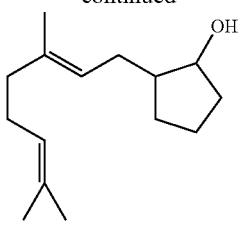

(E)-2-(3,7-dimethylocta-2,6-dienyl)cyclopentanol
Chemical Formula: $C_{15}H_{26}O$
Molecular Weight: 222.37
Apritol

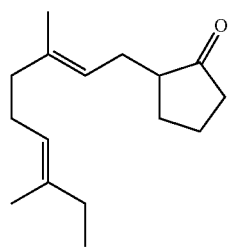

2-((2E,6E)-3,7-dimethylnona-2,6-dienyl)cyclopentanone
Chemical Formula: $C_{16}H_{26}O$
Molecular Weight: 234.38
Methyl Apritone

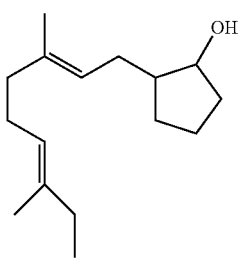

2-((2E,6E)-3,7-dimethylnona-2,6-dienyl)cyclopentanol
Chemical Formula: $C_{16}H_{28}O$
Molecular Weight: 236.39
Methyl Apritol

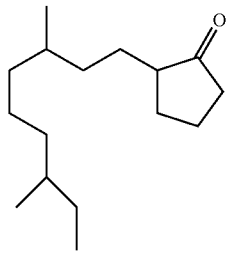 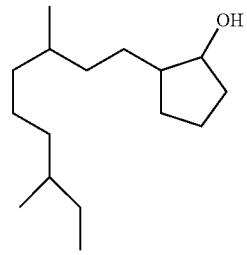

2-(3,7-dimethylnonyl)cyclopentanone    2-(3,7-dimethylnonyl)cyclopentanol
Chemical Formula: $C_{16}H_{30}O$          Chemical Formula: $C_{16}H_{32}O$
Molecular Weight: 238.41               Molecular Weight: 240.42
Tetrahydromethyl Apritone              Tetrahydromethyl Apritol

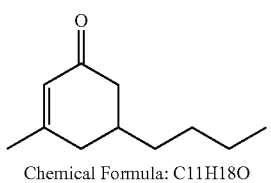 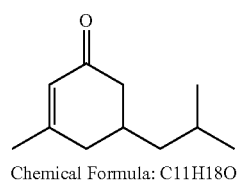

Chemical Formula: $C_{11}H_{18}O$          Chemical Formula: $C_{11}H_{18}O$
Molecular Weight: 166.26               Molecular Weight: 166.26
3-methyl-5-butyl-2-cyclohexenone       3-methyl-5-isobutyl-2-cyclohexenone -continued

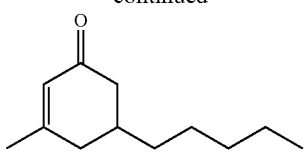

Chemical Formula: C12H20O
Molecular Weight: 180.29
3-methyl-5-pentyl-2-cyclohexenone

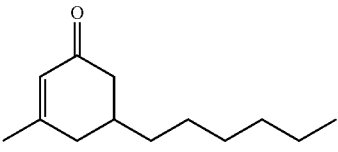

Chemical Formula: C13H22O
Molecular Weight: 194.31
3-methyl-5-hexyl-2-cyclohexenone

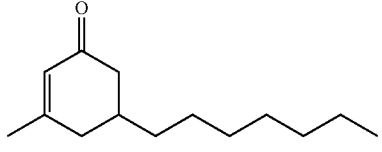

Chemical Formula: C14H24O
Molecular Weight: 208.34
3-methyl-5-heptyl-2-cyclohexenone

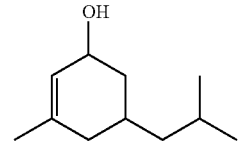

Chemical Formula: C11H20O
Molecular Weight: 168.28
3-methyl-5-isobutyl-2-cyclohexen-1-ol

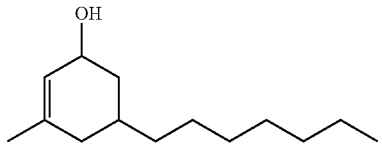

3-methyl-5-heptyl-2-cyclohexen-1-ol
Chemical Formula: C14H26O
Molecular Weight: 210.36

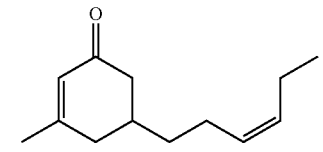

Chemical Formula: C13H20O
Molecular Weight: 192.30
3-methyl-5-(z-3-hexenyl)-2-cyclohexenone

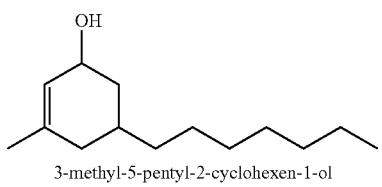

3-methyl-5-pentyl-2-cyclohexen-1-ol
Chemical Formula: C12H22O
Molecular Weight: 182.30

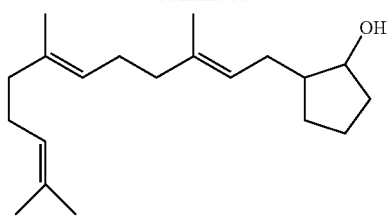

2-((2E,6E)-3,7,11-trimethyldodeca-2,6,10-trienyl)cyclopentanol
Chemical Formula: $C_{20}H_{34}O$
Molecular Weight: 290.48
Farnesylcyclopentanol

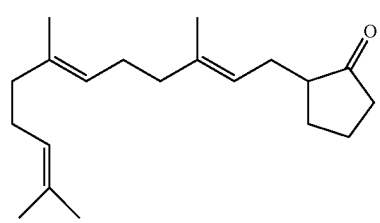

2-((2E,6E)-3,7,11-trimethyldodeca-2,6,10-trienyl)cyclopentanone
Chemical Formula: $C_{20}H_{32}O$
Molecular Weight: 288.47
Farnesylcyclopentanone

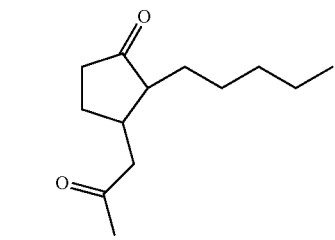

3-(2-oxopropyl)-2-pentylcyclopentanone
Chemical Formula: $C_{13}H_{22}O_2$
Molecular Weight: 210.31
Amyl Cyclopentanone Propanone

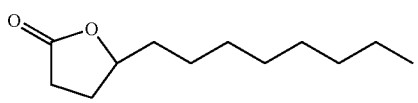

5-octyldihydrofuran-2(3H)-one
Chemical Formula: $C_{12}H_{22}O_2$
Molecular Weight: 198.30
gamma-dodecalactone

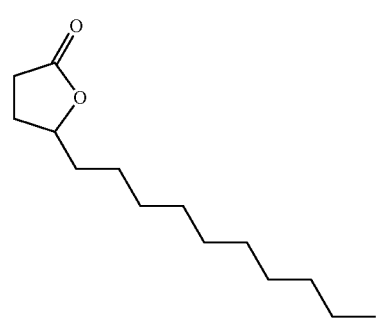

5-decyldihydrofuran-2(3H)-one
Chemical Formula: $C_{14}H_{26}O_2$
Molecular Weight: 226.36
Gamma-Tetradecalactone

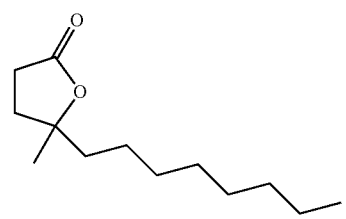

6-nonyltetrahydro-2H-pyran-2-one
Chemical Formula: $C_{14}H_{26}O_2$
Molecular Weight: 226.36
Delta-Tetradecalactone

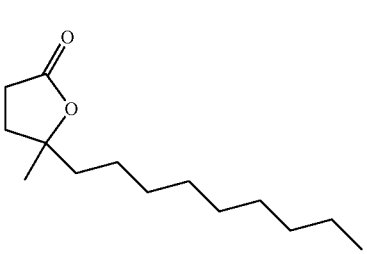

Gamma Methyl Dodecalactone
2(3H)-Furanone, 5-octyldihydro-5-methyl-

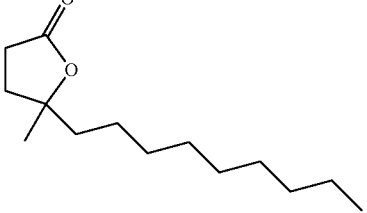

gamma Methyl Tridecalactone
5-methyl-5-nonyldihydrofuran-2(3H)-one
4-methyl-4-nonyl gamma butyrolactone
C14 latone

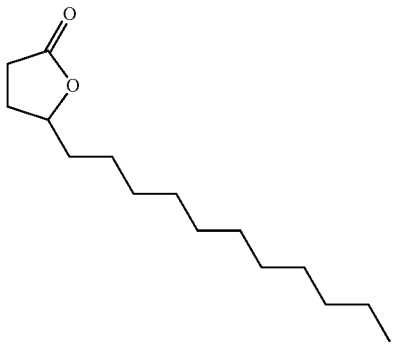

Chemical Formula: $C_{15}H_{28}O_2$
Molecular Weight: 240.38
Gamma Pentadecalactone

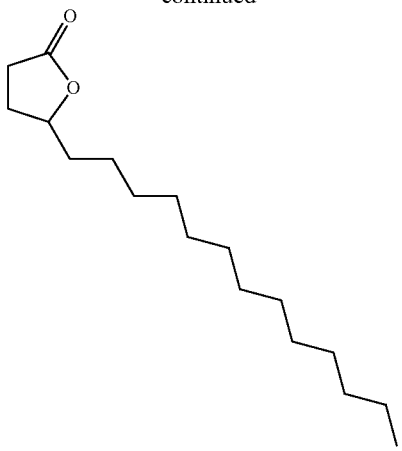

gamma Heptadecalactone
Chemical Formula: $C_{17}H_{32}O_2$
Molecular Weight: 268.24

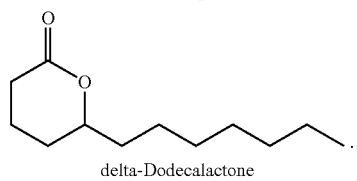

delta-Dodecalactone

Especially preferred compounds of structure (A) of compounds (a) include methyl apritone, methyl dihydrojasmonate, propyl dihydrojasmonate, gamma-dodecalactone, delta-dodecalactone, gamma-tridecalactone, gamma-tetradecalactone, gamma methyl dodecalactone, gamma methyl tridecalactone, 3-methyl-5-pentyl-2-cyclohexenone, 3-methyl-5-pentyl-2-cyclohexenol, 3-methyl-5-hexyl-2-cyclohexenone, and 3-methyl-5-heptyl-2-cyclohexenone.

Representative examples of carboxylic acids of compounds (a) include, but are not limited to, lactic acid, salicylic acid, geranic acid, citronellic acid, 3-methyl-2-decenoic acid, and any isomers thereof. Preferred carboxylic acids of compounds (a) include the following having the formula:

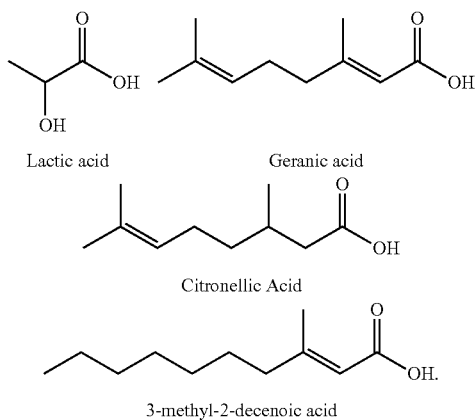

Lactic acid

Geranic acid

Citronellic Acid 3-methyl-2-decenoic acid

Representative examples of esters of carboxylic acids of compounds (a) include, but are not limited to, methyl lactate, ethyl lactate, propyl lactate, butyl lactate, amyl lactate, isoamyl lactate, hexyl lactate, cis-3-hexenyl lactate, methyl geranate, ethyl geranate, isoamyl geranate, methyl citronellate, ethyl citronellate, methyl salicylate, ethyl salicylate, amyl salicylate, isoamyl salicylate, hexyl salicylate, cis-3-hexenyl salicylate, and any isomers thereof.

The formulations of this disclosure may be employed against any biting arthropod desired to be repelled or controlled. Such biting arthropods and insects include mosquitoes, bed bugs, biting flies, ticks, ants, fleas, biting midges, and spiders. Preferably, the formulations are employed against ticks, mosquitoes and bed bugs.

In addition, the active control agents of this disclosure can be effective control agent against biting flies, house flies, ticks, ants, fleas, biting midges, cockroaches, spiders and stink bugs. Biting flies include but are not limited to sand files, stable flies, deer flies, horse flies, black flies and biting midges. House flies include but are not limited to common house flies and lesser house flies. Examples of ticks include but are not limited to deer ticks, lone star ticks and brown dog ticks. Ants include but are not limited to carpenter ants, bullet ants, Jack jumper ants, Pharaoh ants and fire ants. Cockroaches include but are not limited to American cockroaches, German cockroaches, Oriental cockroaches and tropical cockroaches. Spiders include, but are not limited to, cob-web spinning spiders like the Black Widow. Stink bugs include but are not limited to the Brown Marmorated Stink Bug, Southern Green Stink Bug, Forest Bug, Harlequin Bug and the Rice Stink Bug.

The synergistic formulations of this disclosure may be any combination of an alkoxy nootkatol, and the one or more compounds (a) and/or the one or more repellents selected from the group consisting of DEET®, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds, that exhibits a synergistic effect against any biting arthropod to be repelled or controlled.

The active compounds of the synergistic formulations may be formulated into any suitable formulations such as for example, including but not limited to, solutions, oils, creams, lotions, shampoos, aerosols or the like. Traditional inert carriers such as, including but not limited to, alcohols, esters and petroleum distillates, could be used to produce formulations of the active compounds to be used as repellent formulations. Another series of carriers are the biodegradable oils, including but not limited to, the Olestra® family of oils, isopropyl myristate and squalane.

When the formulation will be used as an aerosol, it is preferable to add a propellant. Suitable propellants include, but are not limited to, propane, butane, isobutane, dimethyl ether, carbon dioxide, nitrous oxide, nitrogen, and combinations thereof.

The total amount of active biting arthropod repellent compound utilized in any biting arthropod control or repellent formulation will depend upon the type of formulation used and the particular biting arthropod against which the formulation is employed but will generally range from about 0.5% to about 30% by weight in a carrier.

The active control compounds of the synergistic formulations may be applied to surfaces of or impregnated in clothing or fabric. The active ingredients may be applied to fabrics such as, but not limited to, mosquito nets. The amount of active material can be about 0.025 $g/ft^2$ to about 3.6 $g/ft^2$.

The formulations of active repellent ingredients may also be applied to outdoor materials such as, but not limited to, lawns, trees, shrubbery, or flooring to prevent the biting arthropods from resting there.

The formulations described above can be prepared by any convenient means, e.g., by mixing the active compound or active compounds with one or more other carriers or vehicles such as, including but not limited to, those described herein before.

The following clauses are preferred embodiments of this disclosure:

1. A method for the control or repellency of biting arthropods, the method comprising bringing the biting arthropods into contact with a biting arthropod repellent formulation, wherein the biting arthropod repellent formulation comprises an alkoxy nootkatol.

2. The method of clause 1 wherein the alkoxy nootkatol is methoxy nootkatol.

3. The method of clause 1 wherein the alkoxy nootkatol is present in an amount from about 0.5 weight percent to about 30 weight percent, based on the total weight of the biting arthropod repellent formulation.

4. The method of clause 1 wherein the biting arthropods comprise ticks, mosquitoes and bed bugs.

5. The method of clause 1 wherein the biting arthropod repellent formulation is applied to the skin in the form of wipes, lotions, creams, oils, or sprays.

6. The method of clause 1 wherein the biting arthropod repellent formulation is applied to cleaning products.

7. A method for the control or repellency of biting arthropods, the method comprising bringing the biting arthropods into contact with a biting arthropod repellent formulation, wherein the biting arthropod repellent formulation comprises:

(I) any combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range;

(2) compounds of the structure (A)

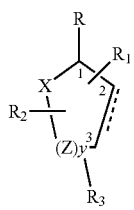

wherein:
R is selected from —OH, =O, —OC(O)R$_4$, —OR$_6$, and —(OR$_6$)$_2$, wherein each R$_6$ is independently selected from an alkyl group containing from about 1 to about 4 carbon atoms and R$_4$ is a branched or straight chain, saturated or unsaturated, hydrocarbyl group with zero to two double bonds and from about 1 to about 15 carbon atoms:
X is O or CH$_2$, with the proviso that when X is O, R, can only be =O:
each Z is independently selected from (CH) and (CH$_2$);
y is a numeral selected from 1 and 2;
R$_1$ is selected from H or a branched or straight chain, saturated or unsaturated, hydrocarbyl group with zero to two double bonds and from about 1 to about 15 carbon atoms:
R$_2$ is selected from H and a branched or straight chain, saturated or unsaturated, hydrocarbyl group with zero to three double bonds and from about 1 to about 15 carbon atoms;
R$_3$ is selected from H, a branched or straight chain, saturated or unsaturated, hydrocarbyl group with zero to three double bonds and from about 1 to about 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, and —CH$_2$C(O)NR$_{11}$R$_{12}$, wherein each of R$_8$, R$_7$, R$_8$, R$_9$, R$_{10}$, R$_{11}$ and R$_{12}$ is independently selected from H and a branched or straight chain, saturated or unsaturated, hydrocarbyl group with zero to three double bonds and from about 1 to about 15 carbon atoms, and n is n integer of from 1 to 12;
the bond between the 2 and 3 positions in the ring structure may be a single or a double bond; and
wherein the compounds of structure (A) contain from about 11 to about 20 carbon atoms except where R is =O, X=CH$_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof; and (4) esters of branched or unbranched, straight chain or cyclic, saturated or unsaturated, carboxylic acids containing from about 3 to about 18 carbon atoms or any range of carbon atoms within said range, including isomers thereof; or (II) any combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds.

8. The method of clause 7 wherein the alkoxy nootkatol is methoxy nootkatol.

9. The method of clause 7 wherein the alkoxy nootkatol is present in an amount from about 0.5 weight percent to about 30 weight percent, and the one or more compounds (a), or the one or more repellents, are present in an amount from about 0.5 weight percent to about 25 weight percent, based on the total weight of the biting arthropod repellent formulation.

10. The method of clause 7 wherein the alkyl and cyclic ketones of compound (a) comprise geranyl acetone (6,10-dimethyl-5,9-undecadien-2-one), farnesyl acetone (5,9,13-pentadecatrien-2-one), 6,10,14-trimethyl-)methyl undecyl ketone (2-tridecanone), methyl decyl ketone (2-dodecanone), alpha-ionone (4-(2,6,6-trimethyl-2-cyclohexenyl)-3-buten-2-one), beta ionone (4-(2,6,6-trimethyl-1-cyclohexenyl)-3-buten-2-one), alpha-isomethylionone (3-methyl-4-(2,6,6-trimethyl-2-cyclohexen-1-yl)-3-buten-2-one), isobutylionone ((E)-5-methyl-1-(2,6,6-trimethyl-1-cyclohex-2-enyl) hex-1-en-3-one), isolongifolen-9-one ((1R)-2,2,7,7-tetramethyltricyclo[6.2.1.01,6]undec-5-en-4-one), dimethylionone ((E)-2-methyl-1-(2,2,6-trimethyl-1-cyclohex-3-enyl)pent-1-en-3-one), isolongifolanone (2,2,7,7-tetramethyltricyclo[6.2.1.01,6]undecan-5-one), pseudoionone (6,10-dimethyl-3,5,9-undecatrien-2-one), 2-cyclopentylcyclopentanone, methyl nonyl ketone (2-undecanone), and 3-decen-2-one.

11. The method of clause 7 wherein the alkyl and cyclic ketones of compound (a) comprise methyl decyl ketone, methyl undecyl ketone, methyl nonyl ketone, geranyl acetone, farnesyl acetone, ionone, and isolongifolenone.

12. The method of clause 7 wherein the compounds of structure (A) of compound (a) comprise compounds having the formula

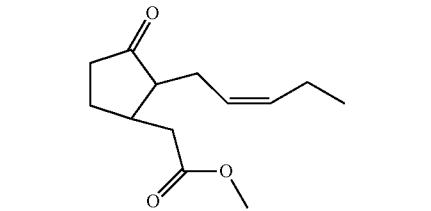

(Z)-methyl 2-(3-oxo-2-(pent-2-enyl)cyclopentyl)acetate
Chemical Formula: $C_{13}H_{20}O_3$
Molecular Weight: 224.30
Methyl Jasmonate

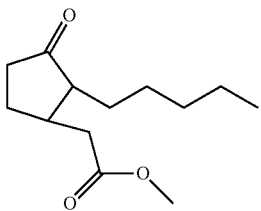

methyl 2-(3-oxo-2-pentylcyclopentyl)acetate
Chemical Formula: $C_{13}H_{22}O_3$
Molecular Weight: 226.31
Methyl Dihydro Jasmonate

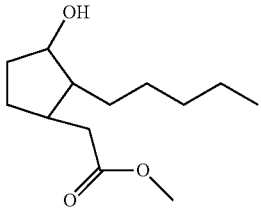

methyl 2-(3-hydroxy-2-pentylcyclopentyl)acetate
Chemical Formula: $C_{13}H_{24}O_3$
Molecular Weight: 228.33
Methyl Dihydro Jasmolate

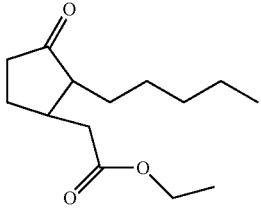

ethyl 2-(3-oxo-2-pentylcyclopentyl)acetate
Chemical Formula: $C_{14}H_{24}O_3$
Molecular Weight: 240.34
Ethyl Dihydro Jasmonate

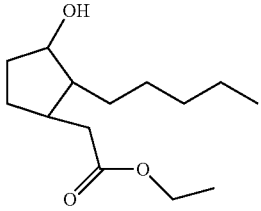

ethyl 2-(3-hydroxy-2-pentylcyclopentyl)acetate
Chemical Formula: $C_{14}H_{26}O_3$
Molecular Weight: 242.35
Ethyl Dihydro Jasmolate

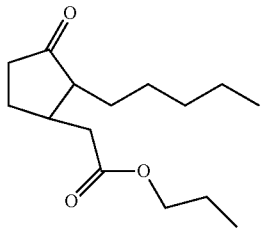

propyl 2-(3-oxo-2-pentylcyclopentyl)acetate
Chemical Formula: $C_{15}H_{26}O_3$
Molecular Weight: 254.37
Propyl Dihydro Jasmonate

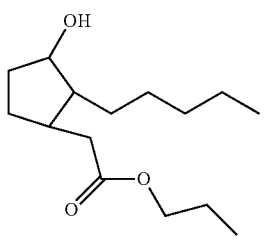

propyl 2-(3-hydroxy-2-pentylcyclopentyl)acetate
Chemical Formula: $C_{15}H_{28}O_3$
Molecular Weight: 256.38
Propyl Dihydro Jasmolate

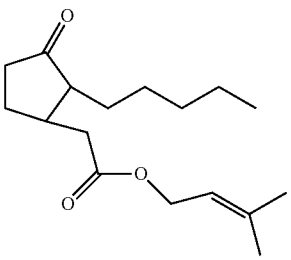

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate

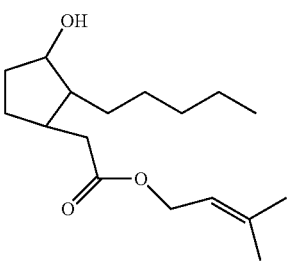

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate -continued

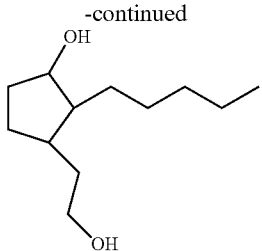

3-(2-hydroxyethyl)-2-pentylcyclopentanol
Chemical Formula: $C_{12}H_{24}O_2$
Molecular Weight: 200.32
MethylDihydroJasmodiol

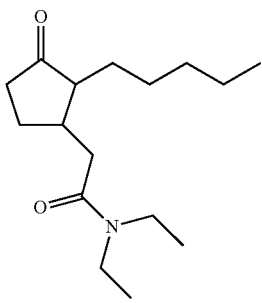

N,N-diethyl-2-(3-oxo-2-pentylcyclopentyl)acetamide
Chemical Formula: $C_{16}H_{29}NO_2$
Molecular Weight: 267.41
MDJ Amide

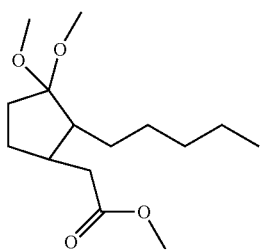

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

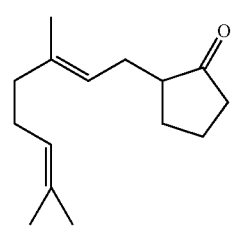

(E)-2-(3,7-dimethylocta-2,6-dienyl)cyclopentanone
Chemical Formula: $C_{15}H_{24}O$
Molecular Weight: 220.35
Apritone -continued

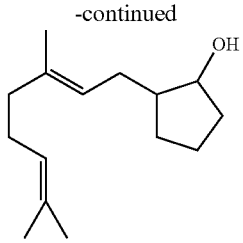

(E)-2-(3,7-dimethylocta-2,6-dienyl)cyclopentanol
Chemical Formula: $C_{15}H_{26}O$
Molecular Weight: 222.37
Apritol

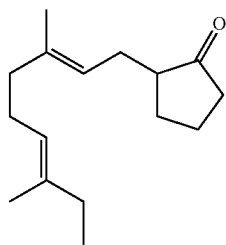

2-((2E,6E)-3,7-dimethylnona-2,6-dienyl)cyclopentanone
Chemical Formula: $C_{16}H_{26}O$
Molecular Weight: 234.38
Methyl Apritone

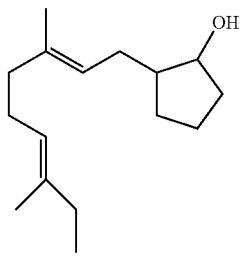

2-((2E,6E)-3,7-dimethylnona-2,6-dienyl)cyclopentanol
Chemical Formula: $C_{16}H_{28}O$
Molecular Weight: 236.39
Methyl Apritol

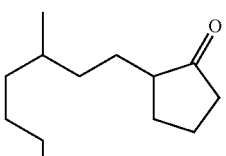 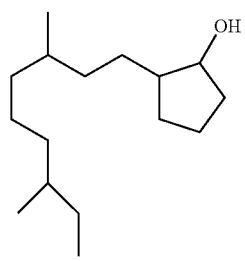

2-(3,7-dimethylnonyl)cyclopentanone  2-(3,7-dimethylnonyl)cyclopentanol
Chemical Formula: $C_{16}H_{30}O$   Chemical Formula: $C_{16}H_{32}O$
Molecular Weight: 238.41           Molecular Weight: 240.42
Tetrahydromethyl Apritone          Tetrahydromethyl Apritol

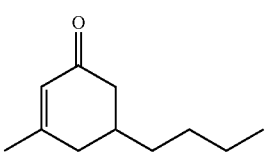 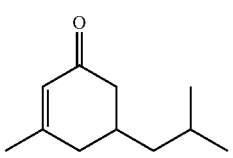

Chemical Formula: C11H18O          Chemical Formula: C11H18O
Molecular Weight: 166.26           Molecular Weight: 166.26
3-methyl-5-butyl-2-cyclohexenone   3-methyl-5-isobutyl-2-cyclohexenone -continued

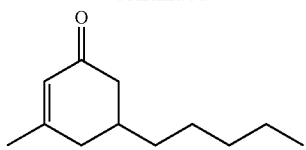

Chemical Formula: C12H20O
Molecular Weight: 180.29
3-methyl-5-pentyl-2-cyclohexenone

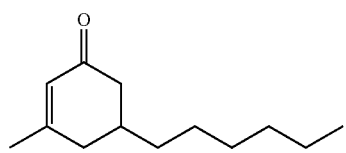

Chemical Formula: C13H22O
Molecular Weight: 194.31
3-methyl-5-hexyl-2-cyclohexenone

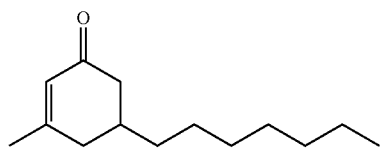

Chemical Formula: C14H24O
Molecular Weight: 208.34
3-methyl-5-heptyl-2-cyclohexenone

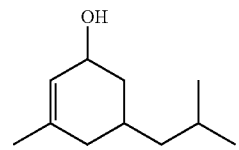

Chemical Formula: C11H20O
Molecular Weight: 168.28
3-methyl-5-isobutyl-2-cyclohexen-1-ol

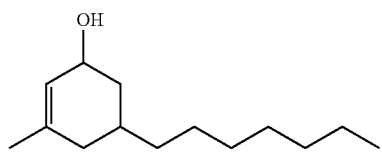

3-methyl-5-heptyl-2-cyclohexen-1-ol
Chemical Formula: C14H26O
Molecular Weight: 210.36

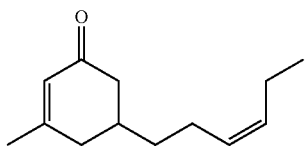

Chemical Formula: C13H20O
Molecular Weight: 192.30
3-methyl-5-(z-3-hexenyl)-2-cyclohexenone

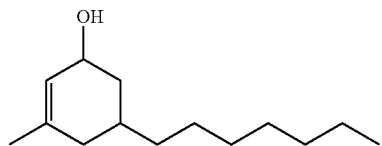

3-methyl-5-pentyl-2-cyclohexen-1-ol
Chemical Formula: C12H22O
Molecular Weight: 182.30

-continued

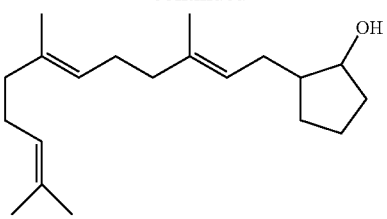

2-((2E,6E)-3,7,11-trimethyldodeca-2,6,10-trienyl)cyclopentanol
Chemical Formula: C20H34O
Molecular Weight: 290.48
Farnesylcyclopentanol

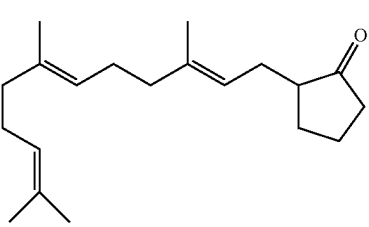

2-((2E,6E)-3,7,11-trimethyldodeca-2,6,10-trienyl)cyclopentanone
Chemical Formula: C20H32O
Molecular Weight: 288.47
Farnesylcyclopentanone

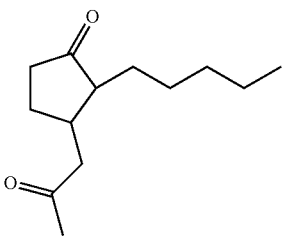

3-(2-oxopropyl)-2-pentylcyclopentanone
Chemical Formula: C13H22O2
Molecular Weight: 210.31
Amyl Cyclopentanone Propanone

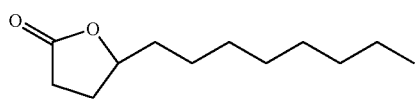

5-octyldihydrofuran-2(3H)-one
Chemical Formula: C12H22O2
Molecular Weight: 198.30
gamma-dodecalactone

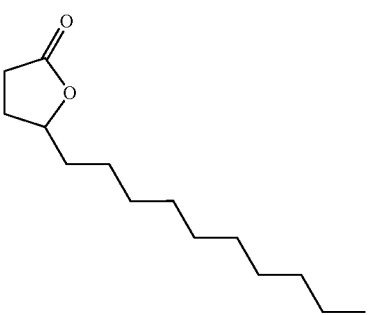

5-decyldihydrofuran-2(3H)-one
Chemical Formula: C14H26O2
Molecular Weight: 226.36
Gamma-Tetradecalactone -continued

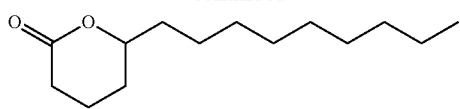

6-nonyltetrahydro-2H-pyran-2-one
Chemical Formula: $C_{14}H_{26}O_2$
Molecular Weight: 226.36
Delta-Tetradecalactone

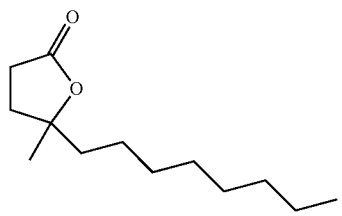

Gamma Methyl Dodecalactone
2(3H)-Furanone, 5-octyldihydro-5-methyl-

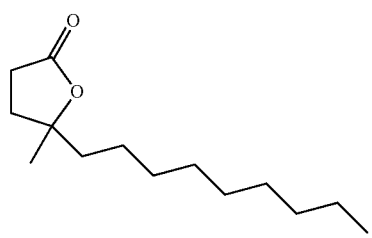

gamma Methyl Tridecalactone
5-methyl-5-nonyldihydrofuran-2(3H)-one
4-methyl-4-nonyl gamma butyrolactone
C14 latone

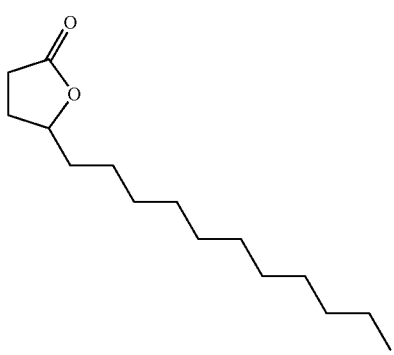

Chemical Formula: $C_{15}H_{28}O_2$
Molecular Weight: 240.38
Gamma Pentadecalactone -continued

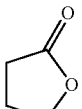

gamma Heptadecalactone
Chemical Formula: $C_{17}H_{32}O_2$
Molecular Weight: 268.24

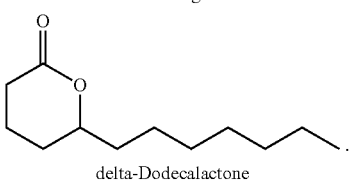

delta-Dodecalactone

13. The method of clause 7 wherein the compounds of structure (A) of compounds (a) comprise methyl apritone, methyl dihydrojasmonate, propyl dihydrojasmonate, gamma-dodecalactone, delta-dodecalactone, gamma-tridecalactone, gamma-tetradecalactone, gamma methyl dodecalactone, gamma methyl tridecalactone, 3-methyl-5-pentyl-2-cyclohexenone, 3-methyl-5-pentyl-2-cyclohexenol, 3-methyl-5-hexyl-2-cyclohexenone, and 3-methyl-5-heptyl-2-cyclohexenone.

14. The method of clause 7 wherein the carboxylic acids of compounds (a) comprise lactic acid, salicylic acid, geranic acid, citronellic acid, 3-methyl-2-decenoic acid, and any isomers thereof.

15. The method of clause 7 wherein the carboxylic acids of compounds (a) comprise lactic acid and isomers thereof.

16. The method of clause 7 wherein the esters of carboxylic acids of compounds (a) comprise methyl lactate, ethyl lactate, propyl lactate, butyl lactate, amyl lactate, isoamyl lactate, hexyl lactate, cis-3-hexenyl lactate, methyl geranate, ethyl geranate, isoamyl geranate, methyl citronellate, ethyl citronellate, methyl salicylate, ethyl salicylate, amyl salicylate, isoamyl salicylate, hexyl salicylate, cis-3-hexenyl salicylate, and any isomers thereof.

17. The method of clause 7 wherein the esters of carboxylic acids of compounds (a) comprise esters of salicylic acid and any isomers thereof.

18. The method of clause 7 wherein the biting arthropod repellent formulation comprises an alkoxy nootkatol, one or more of the compounds (a), and one or more of the repellents.

19. The method of clause 7 wherein the biting arthropod repellent formulation comprises an alkoxy nootkatol and two or more of the compounds (a), or an alkoxy nootkatol and two or more of the repellents.

20. The method of clause 7 wherein the biting arthropods comprise ticks, mosquitoes and bed bugs.

21. The method of clause 7 wherein the biting arthropod repellent formulation is applied to the skin in the form of wipes, lotions, creams, oils, or sprays.

22. The method of clause 7 wherein the biting arthropod repellent formulation is applied to cleaning products.

23. A method for the control or repellency of biting arthropods, the method comprising bringing the biting arthropods into contact with a synergistic biting arthropod repellent formulation, wherein the synergistic biting arthropod repellent formulation comprises:

(I) any synergistic combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range;

(2) compounds of the structure (A)

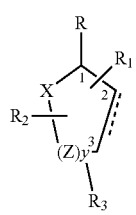

(A)

wherein:
R is selected from —OH, =O, —OC(O)R$_4$, —OR$_6$, and —(OR$_6$)$_2$, wherein each R$_6$ is independently selected from an alkyl group containing from about 1 to about 4 carbon atoms and R$_4$ is a branched or straight chain, saturated or unsaturated, hydrocarbyl group with zero to two double bonds and from about 1 to about 15 carbon atoms:
X is O or CH$_2$, with the proviso that when X is O, R, can only be =O;
each Z is independently selected from (CH) and (CH$_2$);
y is a numeral selected from 1 and 2;
R$_1$ is selected from H or a branched or straight chain, saturated or unsaturated, hydrocarbyl group with zero to two double bonds and from about 1 to about 15 carbon atoms;
R$_2$ is selected from H and a branched or straight chain, saturated or unsaturated, hydrocarbyl group with zero to three double bonds and from about 1 to about 15 carbon atoms;
R$_3$ is selected from H, a branched or straight chain, saturated or unsaturated, hydrocarbyl group with zero to three double bonds and from about 1 to about 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, and —CH$_2$C(O)NR$_{11}$R$_{12}$, wherein each of R$_5$, R$_7$, R$_8$, R$_9$, R$_{10}$, R$_{11}$ and R$_{12}$ is independently selected from H and a branched or straight chain, saturated or unsaturated, hydrocarbyl group with zero to three double bonds and from about 1 to about 15 carbon atoms, and n is n integer of from 1 to 12;
the bond between the 2 and 3 positions in the ring structure may be a single or a double bond; and
wherein the compounds of structure (A) contain from about 11 to about 20 carbon atoms except where R is =O, X=CH$_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof; and (4) esters of branched or unbranched, straight chain or cyclic, saturated or unsaturated, carboxylic acids containing from about 3 to about 18 carbon atoms or any range of carbon atoms within said range, including isomers thereof; or (II) any synergistic combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds:
wherein the synergistic combination of the alkoxy nootkatol in combination with the one or more of compounds (a) and/or the synergistic combination of the alkoxy nootkatol in combination with the one or more repellents, produces a combined effect greater than the sum of their separate effects.

24. The method of clause 23 wherein the alkoxy nootkatol is methoxy nootkatol.

25. The method of clause 23 wherein the alkoxy nootkatol is present in a synergistic amount from about 0.5 weight percent to about 30 weight percent, and the one or more compounds (a), or the one or more repellents, are present in a synergistic amount from about 0.5 weight percent to about 25 weight percent, based on the total weight of the synergistic biting arthropod repellent formulation.

26. The method of clause 23 wherein the alkyl and cyclic ketones of compound (a) comprise geranyl acetone (6,10-dimethyl-5,9-undecadien-2-one), farnesyl acetone (5,9,13-pentadecatrien-2-one), 6,10,14-trimethyl-)methyl undecyl ketone (2-tridecanone), methyl decyl ketone (2-dodecanone), alpha-ionone (4-(2,6,6-trimethyl-2-cyclohexenyl)-3-buten-2-one), beta ionone (4-(2,6,6-trimethyl-1-cyclohexenyl)-3-buten-2-one), alpha-isomethylionone (3-methyl-4-(2,6,6-trimethyl-2-cyclohexen-1-yl)-3-buten-2-one), isobutylionone ((E)-5-methyl-1-(2,6,6-trimethyl-1-cyclohex-2-enyl) hex-1-en-3-one), isolongifolen-9-one ((1R)-2,2,7,7-tetramethyltricyclo[6.2.1.01,6]undec-5-en-4-one), dimethylionone ((E)-2-methyl-1-(2,2,6-trimethyl-1-cyclohex-3-enyl)pent-1-en-3-one), isolongifolanone (2,2,7,7-tetramethyltricyclo[6.2.1.01.6]undecan-5-one), pseudoionone (6,10-dimethyl-3,5,9-undecatrien-2-one), 2-cyclopentylcyclopentanone, methyl nonyl ketone (2-undecanone), and 3-decen-2-one.

27. The method of clause 23 wherein the alkyl and cyclic ketones of compound (a) comprise methyl decyl ketone, methyl undecyl ketone, methyl nonyl ketone, geranyl acetone, farnesyl acetone, ionone, and isolongifolenone.

28. The method of clause 23 wherein the compounds of structure (A) of compound (a) comprise compounds having the formula

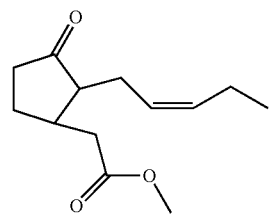

(Z)-methyl 2-(3-oxo-2-(pent-2-enyl)cyclopentyl)acetate
Chemical Formula: C$_{13}$H$_{20}$O$_3$
Molecular Weight: 224.30
Methyl Jasmonate -continued

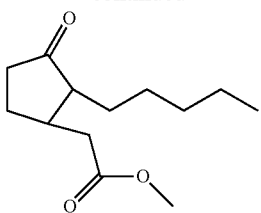

methyl 2-(3-oxo-2-pentylcyclopentyl)acetate
Chemical Formula: $C_{13}H_{22}O_3$
Molecular Weight: 226.31
Methyl Dihydro Jasmonate

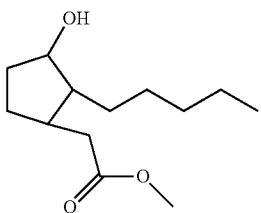

methyl 2-(3-hydroxy-2-pentylcyclopentyl)acetate
Chemical Formula: $C_{13}H_{24}O_3$
Molecular Weight: 228.33
Methyl Dihydro Jasmonate

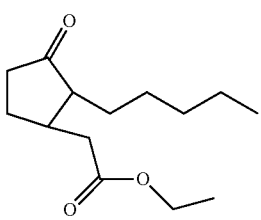

ethyl 2-(3-oxo-2-pentylcyclopentyl)acetate
Chemical Formula: $C_{14}H_{24}O_3$
Molecular Weight: 240.34
Ethyl Dihydro Jasmonate

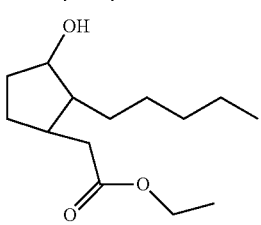

ethyl 2-(3-hydroxy-2-pentylcyclopentyl)acetate
Chemical Formula: $C_{14}H_{26}O_3$
Molecular Weight: 242.35
Ethyl Dihydro Jasmonate

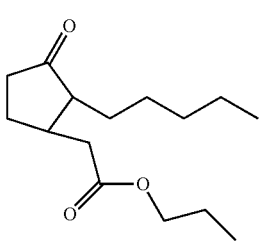

propyl 2-(3-oxo-2-pentylcyclopentyl)acetate
Chemical Formula: $C_{15}H_{26}O_3$
Molecular Weight: 254.37
Propyl Dihydro Jasmonate -continued

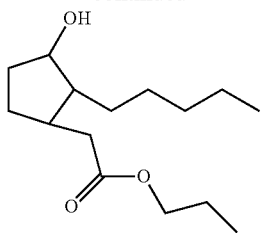

propyl 2-(3-hydroxy-2-pentylcyclopentyl)acetate
Chemical Formula: $C_{15}H_{28}O_3$
Molecular Weight: 256.38
Propyl Dihydro Jasmolate

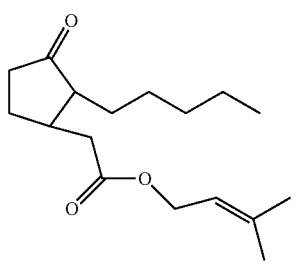

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate

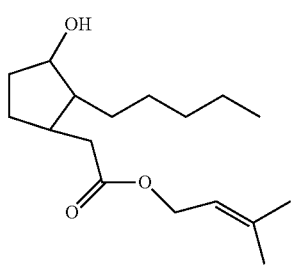

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate

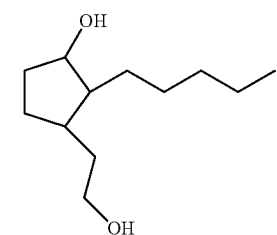

3-(2-hydroxyethyl)-2-pentylcyclopentanol
Chemical Formula: $C_{12}H_{24}O_2$
Molecular Weight: 200.32
MethylDihydroJasmodiol -continued

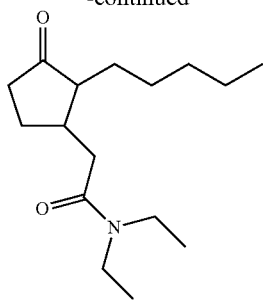

N,N-diethyl-2-(3-oxo-2-pentylcyclopentyl)acetamide
Chemical Formula: $C_{16}H_{29}NO_2$
Molecular Weight: 267.41
MDJ Amide

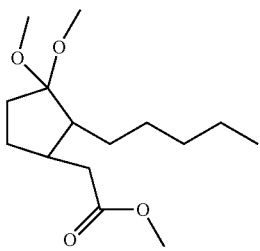

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

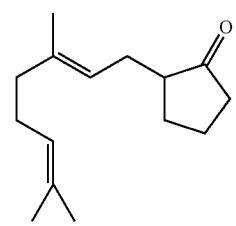

(E)-2-(3,7-dimethylocta-2,6-dienyl)cyclopentanone
Chemical Formula: $C_{15}H_{24}O$
Molecular Weight: 220.35
Apritone

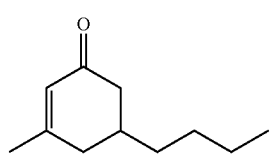

(E)-2-(3,7-dimethylocta-2,6-dienyl)cyclopentanol
Chemical Formula: $C_{15}H_{26}O$
Molecular Weight: 222.37
Apritol -continued

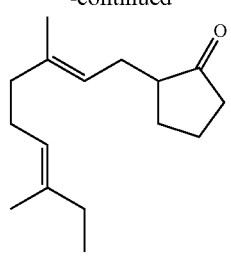

2-((2E,6E)-3,7-dimethylnona-2,6-dienyl)cyclopentanone
Chemical Formula: $C_{16}H_{26}O$
Molecular Weight: 234.38
Methyl Apritone

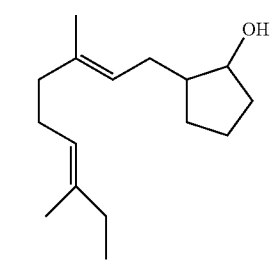

2-((2E,6E)-3,7-dimethylnona-2,6-dienyl)cyclopentanol
Chemical Formula: $C_{16}H_{28}O$
Molecular Weight: 236.39
Methyl Apritol

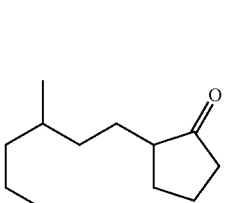 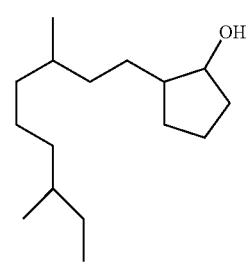

2-(3,7-dimethylnonyl)cyclopentanone    2-(3,7-dimethylnonyl)cyclopentanol
Chemical Formula: $C_{16}H_{30}O$          Chemical Formula: $C_{16}H_{32}O$
Molecular Weight: 238.41               Molecular Weight: 240.42
Tetrahydromethyl Apritone              Tetrahydromethyl Apritol

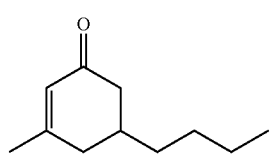 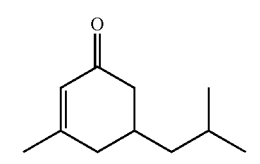

Chemical Formula: C11H18O              Chemical Formula: C11H18O
Molecular Weight: 166.26               Molecular Weight: 166.26
3-methyl-5-butyl-2-cyclohexenone       3-methyl-5-isobutyl-2-cyclohexenone

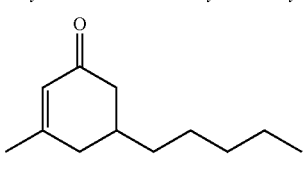

Chemical Formula: C12H20O
Molecular Weight: 180.29
3-methyl-5-pentyl-2-cyclohexenone

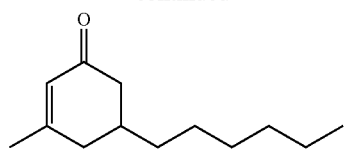

Chemical Formula: C13H22O
Molecular Weight: 194.31
3-methyl-5-hexyl-2-cyclohexenone

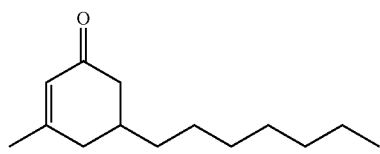

Chemical Formula: C14H24O
Molecular Weight: 208.34
3-methyl-5-heptyl-2-cyclohexenone

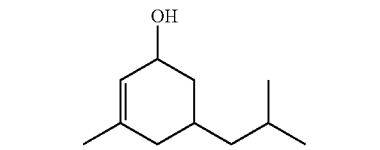

Chemical Formula: C11H20O
Molecular Weight: 168.28
3-methyl-5-isobutyl-2-cyclohexen-1-ol

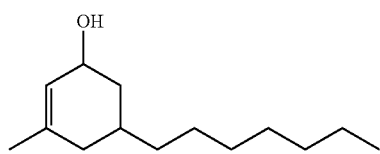

3-methyl-5-heptyl-2-cyclohexen-1-ol
Chemical Formula: C14H26O
Molecular Weight: 210.36

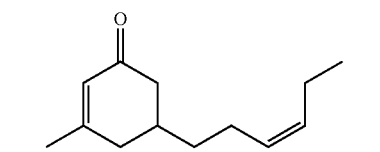

Chemical Formula: C13H20O
Molecular Weight: 192.30
3-methyl-5-(z-3-hexenyl)-2-cyclohexenone

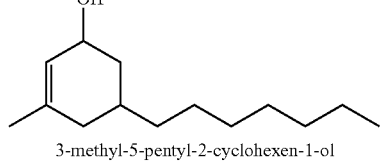

3-methyl-5-pentyl-2-cyclohexen-1-ol
Chemical Formula: C12H22O
Molecular Weight: 182.30

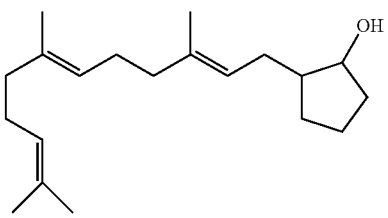

2-((2E,6E)-3,7,11-trimethyldodeca-2,6,10-trienyl)cyclopentanol
Chemical Formula: C20H34O
Molecular Weight: 290.48
Farnesylcyclopentanol

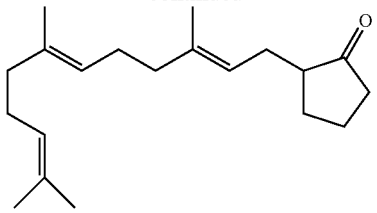

2-((2E,6E)-3,7,11-trimethyldodeca-2,6,10-trienyl)cyclopentanone
Chemical Formula: C20H32O
Molecular Weight: 288.47
Farnesylcyclopentanone

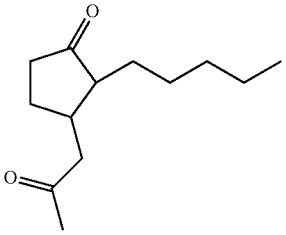

3-(2-oxopropyl)-2-pentylcyclopentanone
Chemical Formula: C13H22O2
Molecular Weight: 210.31
Amyl Cyclopentanone Propanone

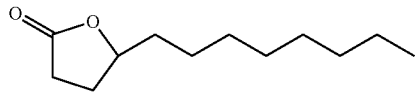

5-octyldihydrofuran-2(3H)-one
Chemical Formula: C12H22O2
Molecular Weight: 198.30
gamma-dodecalactone

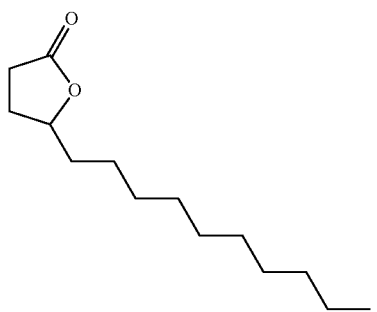

5-decyldihydrofuran-2(3H)-one
Chemical Formula: C14H26O2
Molecular Weight: 226.36
Gamma-Tetradecalactone

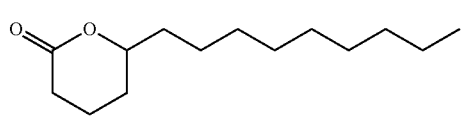

6-nonyltetrahydro-2H-pyran-2-one
Chemical Formula: C14H26O2
Molecular Weight: 226.36
Delta-Tetradecalactone -continued

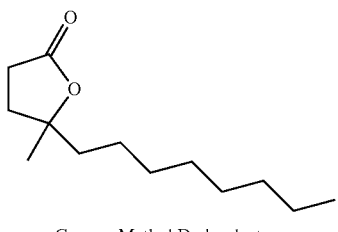

Gamma Methyl Dodecalactone
2(3H)-Furanone, 5-octyldihydro-5-methyl-

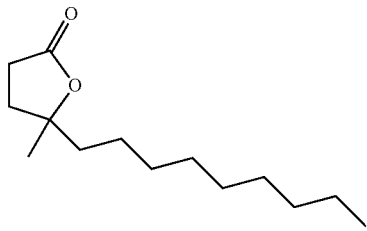

gamma Methyl Tridecalactone
5-methyl-5-nonyldihydrofuran-2(3H)-one
4-methyl-4-nonyl gamma butyrolactone
C14 latone

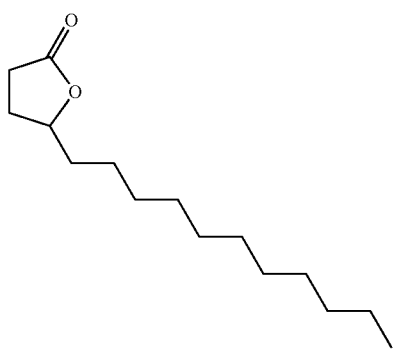

Chemical Formula: $C_{15}H_{28}O_2$
Molecular Weight: 240.38
Gamma Pentadecalactone

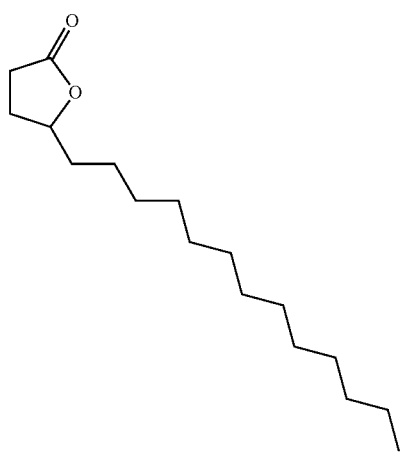

gamma Heptadecalactone
Chemical Formula: $C_{17}H_{32}O_2$
Molecular Weight: 268.24

-continued

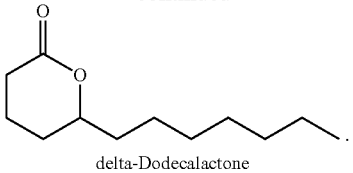

delta-Dodecalactone

29. The method of clause 23 wherein the compounds of structure (A) of compounds (a) comprise methyl apritone, methyl dihydrojasmonate, propyl dihydrojasmonate, gamma-dodecalactone, delta-dodecalactone, gamma-tridecalactone, gamma-tetradecalactone, gamma methyl dodecalactone, gamma methyl tridecalactone, 3-methyl-5-pentyl-2-cyclohexenone, 3-methyl-5-pentyl-2-cyclohexenol, 3-methyl-5-hexyl-2-cyclohexenone, and 3-methyl-5-heptyl-2-cyclohexenone.

30. The method of clause 23 wherein the carboxylic acids of compounds (a) comprise lactic acid, salicylic acid, geranic acid, citronellic acid, 3-methyl-2-decenoic acid, and any isomers thereof.

31. The method of clause 23 wherein the carboxylic acids of compounds (a) comprise lactic acid and isomers thereof.

32. The method of clause 23 wherein the esters of carboxylic acids of compounds (a) comprise methyl lactate, ethyl lactate, propyl lactate, butyl lactate, amyl lactate, isoamyl lactate, hexyl lactate, cis-3-hexenyl lactate, methyl geranate, ethyl geranate, isoamyl geranate, methyl citronellate, ethyl citronellate, methyl salicylate, ethyl salicylate, amyl salicylate, isoamyl salicylate, hexyl salicylate, cis-3-hexenyl salicylate, and any isomers thereof.

33. The method of clause 23 wherein the esters of carboxylic acids of compounds (a) comprise esters of salicylic acid and any isomers thereof.

34. The method of clause 23 wherein the synergistic biting arthropod repellent formulation comprises an alkoxy nootkatol, one or more of the compounds (a), and one or more of the repellents.

35. The method of clause 23 wherein the synergistic biting arthropod repellent formulation comprises an alkoxy nootkatol and two or more of the compounds (a), or an alkoxy nootkatol and two or more of the repellents.

36. The method of clause 23 wherein the biting arthropods comprise ticks, mosquitoes and bed bugs.

37. The method of clause 23 wherein the synergistic biting arthropod repellent formulation is applied to the skin in the form of wipes, lotions, creams, oils, or sprays.

38. The method of clause 23 wherein the synergistic biting arthropod repellent formulation is applied to cleaning products.

39. The method of clause 23 wherein the combined effect is greater repellency or protection time.

40. A biting arthropod repellent formulation comprising an alkoxy nootkatol.

41. The biting arthropod repellent formulation of clause 40 wherein the alkoxy nootkatol is methoxy nootkatol.

42. The biting arthropod repellent formulation of clause 40 wherein the alkoxy nootkatol is present in an amount from about 0.5 weight percent to about 30 weight percent, based on the total weight of the biting arthropod repellent formulation.

43. The biting arthropod repellent formulation of clause 40 wherein the biting arthropods comprise ticks, mosquitoes and bed bugs.

44. The biting arthropod repellent formulation of clause 40 which is applied to the skin in the form of wipes, lotions, creams, oils, or sprays.

45. The biting arthropod repellent formulation of clause 40 which is applied to cleaning products.

46. A biting arthropod repellent formulation comprising:

(I) any combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range;

(2) compounds of the structure (A)

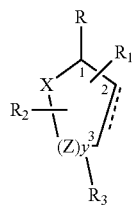

(A)

wherein:

R is selected from —OH, =O, —OC(O)$R_4$, —$OR_6$, and —$(OR_6)_2$, wherein each $R_6$ is independently selected from an alkyl group containing from about 1 to about 4 carbon atoms and $R_4$ is a branched or straight chain, saturated or unsaturated, hydrocarbyl group with zero to two double bonds and from about 1 to about 15 carbon atoms;

X is O or $CH_2$, with the proviso that when X is O, R, can only be =O;

each Z is independently selected from (CH) and ($CH_2$);

v is a numeral selected from 1 and 2;

$R_1$ is selected from H or a branched or straight chain, saturated or unsaturated, hydrocarbyl group with zero to two double bonds and from about 1 to about 15 carbon atoms:

$R_2$ is selected from H and a branched or straight chain, saturated or unsaturated, hydrocarbyl group with zero to three double bonds and from about 1 to about 15 carbon atoms;

$R_3$ is selected from H, a branched or straight chain, saturated or unsaturated, hydrocarbyl group with zero to three double bonds and from about 1 to about 15 carbon atoms, —$(CH_2)_n$OH, —C(O)$OR_5$, —$CH_2$C(O)$OR_7$, —$CH_2$C(O)$R_8$, —C(O)$NR_9R_{10}$, and —$CH_2$C(O)$NR_{11}R_{12}$, wherein each of $R_8$, $R_7$, $R_8$, $R_9$, $R_{10}$, $R_{11}$ and $R_{12}$ is independently selected from H and a branched or straight chain, saturated or unsaturated, hydrocarbyl group with zero to three double bonds and from about 1 to about 15 carbon atoms, and n is n integer of from 1 to 12:

the bond between the 2 and 3 positions in the ring structure may be a single or a double bond; and wherein the compounds of structure (A) contain from about 11 to about 20 carbon atoms except where R is =O, X=$CH_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof; and (4) esters of branched or unbranched, straight chain or cyclic, saturated or unsaturated, carboxylic acids containing from about 3 to about 18 carbon atoms or any range of carbon atoms within said range, including isomers thereof; or (II) any combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl) amino]propanoate (IR3535), and other nitrogen-containing repellents including amines, amides, and nitrogen-containing heterocyclic compounds.

47. The biting arthropod repellent formulation of clause 46 wherein the alkoxy nootkatol is methoxy nootkatol.

48. The biting arthropod repellent formulation of clause 46 wherein the alkoxy nootkatol is present in an amount from about 0.5 weight percent to about 30 weight percent, and the one or more compounds (a), or the one or more repellents, are present in an amount from about 0.5 weight percent to about 25 weight percent, based on the total weight of the biting arthropod repellent formulation.

49. The biting arthropod repellent formulation of clause 46 wherein the alkyl and cyclic ketones of compound (a) comprise geranyl acetone (6,10-dimethyl-5,9-undecadien-2-one), farnesyl acetone (5,9,13-pentadecatrien-2-one), 6,10,14-trimethyl-)methyl undecyl ketone (2-tridecanone), methyl decyl ketone (2-dodecanone), alpha-ionone (4-(2,6,6-trimethyl-2-cyclohexenyl)-3-buten-2-one), beta ionone (4-(2,6,6-trimethyl-1-cyclohexenyl)-3-buten-2-one), alpha-isomethylionone (3-methyl-4-(2,6,6-trimethyl-2-cyclohexen-1-yl)-3-buten-2-one), isobutylionone ((E)-5-methyl-1-(2,6,6-trimethyl-1-cyclohex-2-enyl) hex-1-en-3-one), isolongifolen-9-one ((1R)-2,2,7,7-tetramethyltricyclo[6.2.1.01,6]undec-5-en-4-one), dimethylionone ((E)-2-methyl-1-(2,2,6-trimethyl-1-cyclohex-3-enyl)pent-1-en-3-one), isolongifolanone (2,2,7,7-tetramethyltricyclo[6.2.1.01,6]undecan-5-one), pseudoionone (6,10-dimethyl-3,5,9-undecatrien-2-one), 2-cyclopentylcyclopentanone, methyl nonyl ketone (2-undecanone), and 3-decen-2-one.

50. The biting arthropod repellent formulation of clause 46 wherein the alkyl and cyclic ketones of compound (a) comprise methyl decyl ketone, methyl undecyl ketone, methyl nonyl ketone, geranyl acetone, farnesyl acetone, ionone, and isolongifolenone.

51. The biting arthropod repellent formulation of clause 46 wherein the compounds of structure (A) of compound (a) comprise compounds having the formula

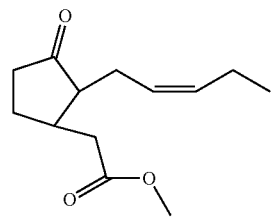

(Z)-methyl 2-(3-oxo-2-(pent-2-enyl)cyclopentyl)acetate
Chemical Formula: $C_{13}H_{20}O_3$
Molecular Weight: 224.30
Methyl Jasmonate -continued

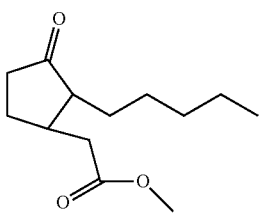

methyl 2-(3-oxo-2-pentylcyclopentyl)acetate
Chemical Formula: $C_{13}H_{22}O_3$
Molecular Weight: 226.31
Methyl Dihydro Jasmonate

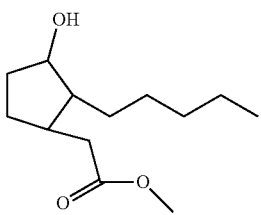

methyl 2-(3-hydroxy-2-pentylcyclopentyl)acetate
Chemical Formula: $C_{13}H_{24}O_3$
Molecular Weight: 228.33
Methyl Dihydro Jasmonate

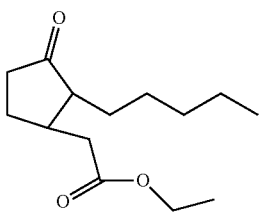

ethyl 2-(3-oxy-2-pentylcyclopentyl)acetate
Chemical Formula: $C_{14}H_{24}O_3$
Molecular Weight: 240.34
Ethyl Dihydro Jasmonate

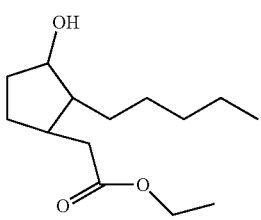

ethyl 2-(3-hydroxy-2-pentylcyclopentyl)acetate
Chemical Formula: $C_{14}H_{26}O_3$
Molecular Weight: 242.35
Ethyl Dihydro Jasmonate

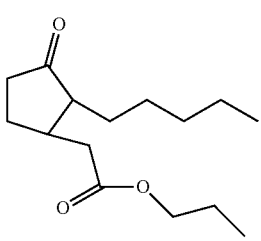

propyl 2-(3-oxo-2-pentylcyclopentyl)acetate
Chemical Formula: $C_{15}H_{26}O_3$
Molecular Weight: 254.37
Propyl Dihydro Jasmonate -continued

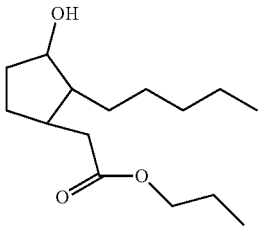

propyl 2-(3-hydroxy-2-pentylcyclopentyl)acetate
Chemical Formula: $C_{15}H_{28}O_3$
Molecular Weight: 256.38
Propyl Dihydro Jasmolate

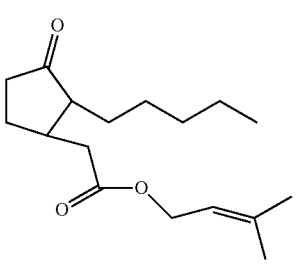

3-methylbut-2-enyl 2-(3-oxo-2-
pentylcyclopentyl)acetate
Chemical Formula: $C_{17}H_{28}O_3$
Molecular Weight: 280.40
Prenyl Dihydro Jasmonate

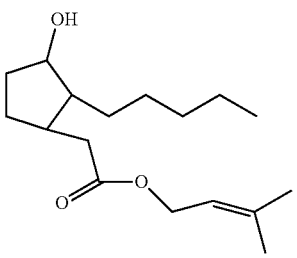

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate

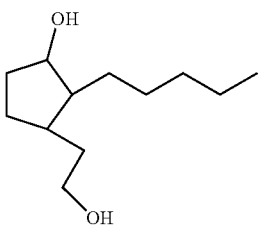

3-(2-hydroxyethyl)-2-pentylcyclopentanol
Chemical Formula: $C_{12}H_{24}O_2$
Molecular Weight: 200.32
MethylDihydroJasmodiol -continued

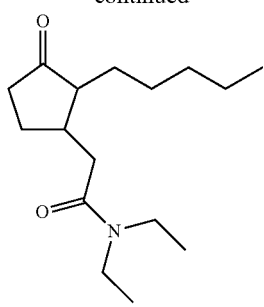

N,N-diethyl-2-(3-oxo-2-pentylcyclopentyl)acetamide
Chemical Formula: $C_{16}H_{29}NO_2$
Molecular Weight: 267.41
MDJ Amide

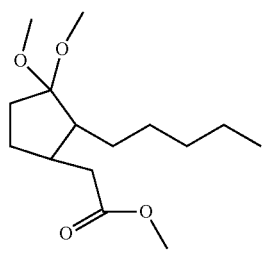

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

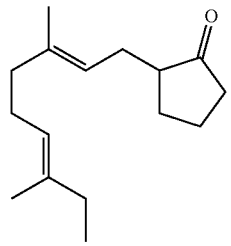

(E)-2-(3,7-dimethylocta-2,6-dienyl)cyclopentanone
Chemical Formula: $C_{15}H_{24}O$
Molecular Weight: 220.35
Apritone

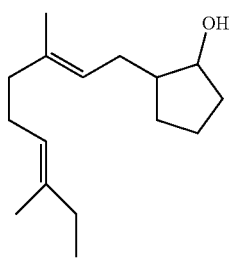

(E)-2-(3,7-dimethylocta-2,6-dienyl)cyclopentanol
Chemical Formula: $C_{15}H_{26}O$
Molecular Weight: 222.37
Apritol -continued

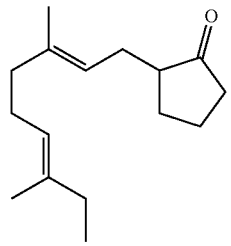

2-((2E,6E)-3,7-dimethylnona-2,6-dienyl)cyclopentanone
Chemical Formula: $C_{16}H_{26}O$
Molecular Weight: 234.38
Methyl Apritone

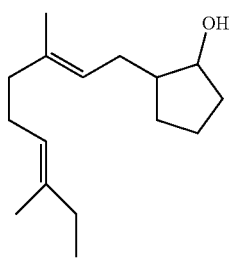

2-((2E,6E)-3,7-dimethylnona-2,6-dienyl)cyclopentanol
Chemical Formula: $C_{16}H_{28}O$
Molecular Weight: 236.39
Methyl Apritol

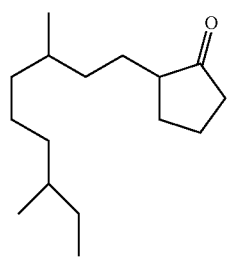

2-(3,7-dimethylnonyl)cyclopentanone
Chemical Formula: $C_{16}H_{30}O$
Molecular Weight: 238.41
Tetrahydromethyl Apritone

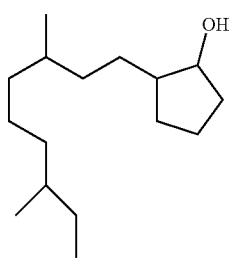

2-(3,7-dimethylnonyl)cyclopentanol
Chemical Formula: $C_{16}H_{32}O$
Molecular Weight: 240.42
Tetrahydromethyl Apritol

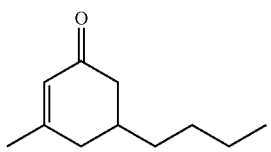

Chemical Formula: C11H18O
Molecular Weight: 166.26
3-methyl-5-butyl-2-cyclohexenone -continued

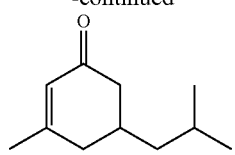

Chemical Formula: C11H18O
Molecular Weight: 166.26
3-methyl-5-isobutyl-2-cyclohexenone

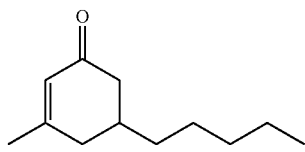

Chemical Formula: C12H20O
Molecular Weight: 180.29
3-methyl-5-pentyl-2-cyclohexenone

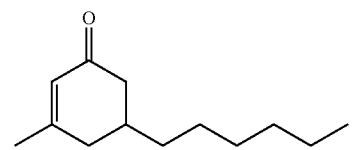

Chemical Formula: C13H22O
Molecular Weight: 194.31
3-methyl-5-hexyl-2-cyclohexenone

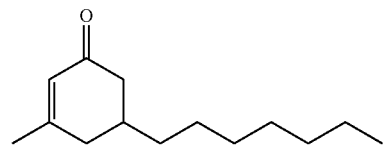

Chemical Formula: C14H24O
Molecular Weight: 208.34
3-methyl-5-heptyl-2-cyclohexenone

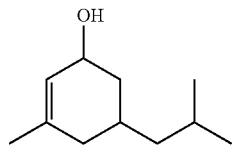

Chemical Formula: C11H20O
Molecular Weight: 168.28
3-methyl-5-isobutyl-2-cyclohexen-1-ol

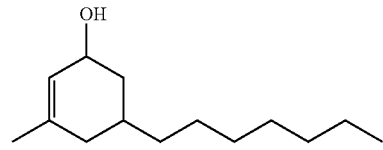

3-methyl-5-heptyl-2-cyclohexen-1-ol
Chemical Formula: C14H26O
Molecular Weight: 210.36

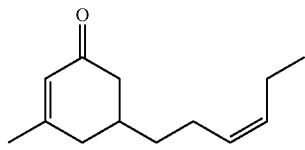

Chemical Formula: C13H20O
Molecular Weight: 192.30
3-methyl-5-(z-3-hexenyl)-2-cyclohexenone -continued

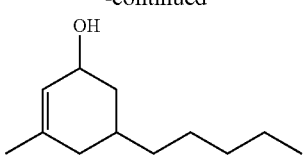

3-methyl-5-pentyl-2-cyclohexen-1-ol
Chemical Formula: C12H22O
Molecular Weight: 182.30

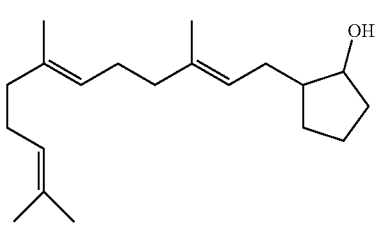

2-((2E,6E)-3,7,11-trimethyldodeca-2,6,10-trienyl)cyclopentanol
Chemical Formula: C20H34O
Molecular Weight: 290.48
Farnesylcyclopentanol

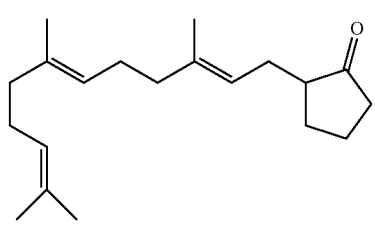

2-((2E,6E)-3,7,11-trimethyldodeca-2,6,10-trienyl)cyclopentanone
Chemical Formula: C20H32O
Molecular Weight: 288.47
Farnesylcyclopentanone

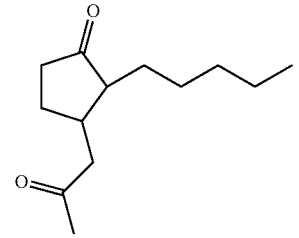

3-(2-oxopropyl)-2-pentylcyclopentanone
Chemical Formula: C13H22O2
Molecular Weight: 210.31
Amyl Cyclopentanone Propanone

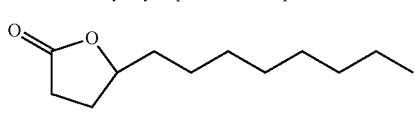

5-octyldihydrofuran-2(3H)-one
Chemical Formula: C12H22O2
Molecular Weight: 198.30
gamma-dodecalactone -continued

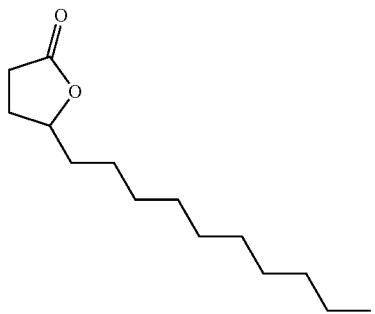

5-decyldihydrofuran-2(3H)-one
Chemical Formula: $C_{14}H_{26}O_2$
Molecular Weight: 226.36
Gamma-Tetradecalactone

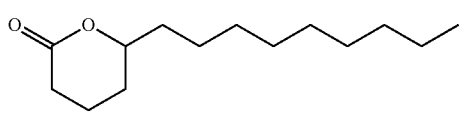

6-nonltetrahydro-2H-pyran-2-one
Chemical Formula: $C_{14}H_{26}O_2$
Molecular Weight: 226.36
Deltra-Tetradecalactone

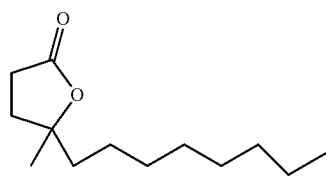

Gamma Methyl Dodecalactone
2(3H)-Furanone, 5-octyldihydro-5-methyl-

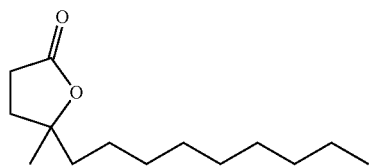

gamma Methyl Tridecalactone
5-methyl-5-nonyldihydrofuran-2(3H)-one
4-methyl-4-nonyl gamma butyrolactone
C14 lactone

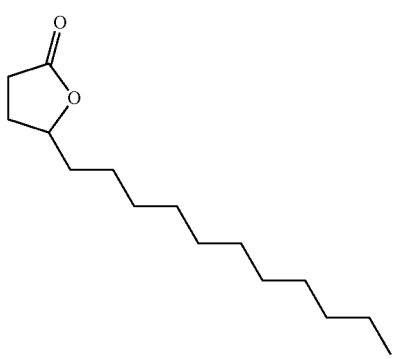

Chemical Formula: $C_{15}H_{28}O_2$
Molecular Weight: 240.38
Gamma Pentadecalactone -continued

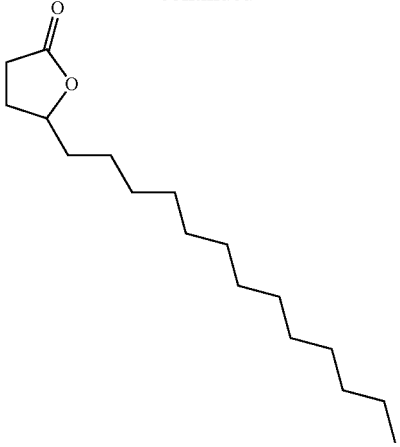

gamma Heptadecalacone
Chemical Formula: $C_{17}H_{32}O_2$
Molecular Weight: 268.24

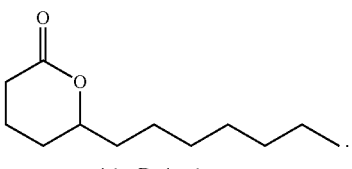

delta-Dodecalactone

52. The biting arthropod repellent formulation of clause 46 wherein the compounds of structure (A) of compounds (a) comprise methyl apritone, methyl dihydrojasmonate, propyl dihydrojasmonate, gamma-dodecalactone, delta-dodecalactone, gamma-tridecalactone, gamma-tetradecalactone, gamma methyl dodecalactone, gamma methyl tridecalactone, 3-methyl-5-pentyl-2-cyclohexenone, 3-methyl-5-pentyl-2-cyclohexenol, 3-methyl-5-hexyl-2-cyclohexenone, and 3-methyl-5-heptyl-2-cyclohexenone.

53. The biting arthropod repellent formulation of clause 46 wherein the carboxylic acids of compounds (a) comprise lactic acid, salicylic acid, geranic acid, citronellic acid, 3-methyl-2-decenoic acid, and any isomers thereof.

54. The biting arthropod repellent formulation of clause 46 wherein the carboxylic acids of compounds (a) comprise lactic acid and isomers thereof.

55. The biting arthropod repellent formulation of clause 46 wherein the esters of carboxylic acids of compounds (a) comprise methyl lactate, ethyl lactate, propyl lactate, butyl lactate, amyl lactate, isoamyl lactate, hexyl lactate, cis-3-hexenyl lactate, methyl geranate, ethyl geranate, isoamyl geranate, methyl citronellate, ethyl citronellate, methyl salicylate, ethyl salicylate, amyl salicylate, isoamyl salicylate, hexyl salicylate, cis-3-hexenyl salicylate, and any isomers thereof.

56. The biting arthropod repellent formulation of clause 46 wherein the esters of carboxylic acids of compounds (a) comprise esters of salicylic acid and any isomers thereof.

57. The biting arthropod repellent formulation of clause 46 which comprises an alkoxy nootkatol, one or more of the compounds (a), and one or more of the repellents.

58. The biting arthropod repellent formulation of clause 46 which comprises an alkoxy nootkatol and two or more of the compounds (a), or an alkoxy nootkatol and two or more of the repellents.

59. The biting arthropod repellent formulation of clause 46 wherein the biting arthropods comprise ticks, mosquitoes and bed bugs.

60. The biting arthropod repellent formulation of clause 46 which is applied to the skin in the form of wipes, lotions, creams, oils, or sprays.

61. The biting arthropod repellent formulation of clause 46 which is applied to cleaning products.

62. A synergistic biting arthropod repellent formulation comprising:

(I) any synergistic combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range;

(2) compounds of the structure (A)

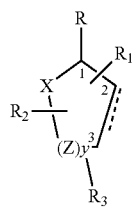

(A)

wherein:
R is selected from —OH, =O, —OC(O)R$_4$, —OR$_6$, and —(OR$_6$)$_2$, wherein each R$_6$ is independently selected from an alkyl group containing from about 1 to about 4 carbon atoms and R$_4$ is a branched or straight chain, saturated or unsaturated, hydrocarbyl group with zero to two double bonds and from about 1 to about 15 carbon atoms;
X is O or CH$_2$, with the proviso that when X is O, R, can only be =O; each Z is independently selected from (CH) and (CH$_2$);
y is a numeral selected from 1 and 2;
R$_1$ is selected from H or a branched or straight chain, saturated or unsaturated, hydrocarbyl group with zero to two double bonds and from about 1 to about 15 carbon atoms;
R$_2$ is selected from H and a branched or straight chain, saturated or unsaturated, hydrocarbyl group with zero to three double bonds and from about 1 to about 15 carbon atoms:
R$_3$ is selected from H, a branched or straight chain, saturated or unsaturated, hydrocarbyl group with zero to three double bonds and from about 1 to about 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, and —CH$_2$C(O)NR$_{11}$R$_{12}$, wherein each of R$_5$, R$_7$, R$_8$, R$_9$, R$_{10}$, R$_{11}$ and R$_{12}$ is independently selected from H and a branched or straight chain, saturated or unsaturated, hydrocarbyl group with zero to three double bonds and from about 1 to about 15 carbon atoms, and n is n integer of from 1 to 12;
the bond between the 2 and 3 positions in the ring structure may be a single or a double bond; and
wherein the compounds of structure (A) contain from about 11 to about 20 carbon atoms except where R is =O, X=CH$_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof; and (4) esters of branched or unbranched, straight chain or cyclic, saturated or unsaturated, carboxylic acids containing from about 3 to about 18 carbon atoms or any range of carbon atoms within said range, including isomers thereof, or (II) any synergistic combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl) amino]propanoate (IR3535), and other nitrogen-containing repellents including amines, amides, and nitrogen-containing heterocyclic compounds;
wherein the synergistic combination of the alkoxy nootkatol in combination with the one or more of compounds (a) and/or the synergistic combination of the alkoxy nootkatol in combination with the one or more repellents, produces a combined effect greater than the sum of their separate effects.

63. The synergistic biting arthropod repellent formulation of clause 62 wherein the alkoxy nootkatol is methoxy nootkatol.

64. The synergistic biting arthropod repellent formulation of clause 62 wherein the alkoxy nootkatol is present in a synergistic amount from about 0.5 weight percent to about 30 weight percent, and the one or more compounds (a), or the one or more repellents, are present in a synergistic amount from about 0.5 weight percent to about 25 weight percent, based on the total weight of the synergistic biting arthropod repellent formulation.

65. The synergistic biting arthropod repellent formulation of clause 62 wherein the alkyl and cyclic ketones of compound (a) comprise geranyl acetone (6,10-dimethyl-5,9-undecadien-2-one), farnesyl acetone (5,9,13-pentadecatrien-2-one), 6,10,14-trimethyl-)methyl undecyl ketone (2-tridecanone), methyl decyl ketone (2-dodecanone), alpha-ionone (4-(2,6,6-trimethyl-2-cyclohexenyl)-3-buten-2-one), beta ionone (4-(2,6,6-trimethyl-1-cyclohexenyl)-3-buten-2-one), alpha-isomethylionone (3-methyl-4-(2,6,6-trimethyl-2-cyclohexen-1-yl)-3-buten-2-one),
isobutylionone ((E)-5-methyl-1-(2,6,6-trimethyl-1-cyclo-hex-2-enyl) hex-1-en-3-one), isolongifolen-9-one ((I R)-2,2,7,7-tetramethyltricyclo[6.2.1.01,6]undec-5-en-4-one),
dimethylionone ((E)-2-methyl-1-(2,2,6-trimethyl-1-cyclo-hex-3-enyl)pent-1-en-3-one), isolongifolanone (2,2,7,7-te-tramethyltricyclo[6.2.1.01,6]undecan-5-one), pseudoionone (6,10-dimethyl-3,5,9-undecatrien-2-one), 2-cyclopentylcy-clopentanone, methyl nonyl ketone (2-undecanone), and 3-decen-2-one.

66. The synergistic biting arthropod repellent formulation of clause 62 wherein the alkyl and cyclic ketones of compound (a) comprise methyl decyl ketone, methyl undecyl ketone, methyl nonyl ketone, geranyl acetone, farnesyl acetone, ionone, and isolongifolenone.

67. The synergistic biting arthropod repellent formulation of clause 62 wherein the compounds of structure (A) of compound (a) comprise compounds having the formula

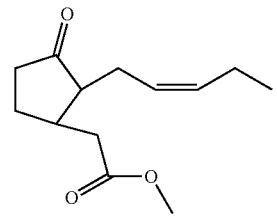

(Z)-methyl 2-(3-oxo-2-(pent-2-enyl)cyclopentyl)acetate
Chemical Formula: $C_{13}H_{20}O_3$
Molecular Weight: 224.30
Methyl Jasmonate

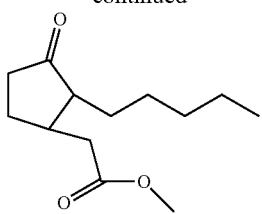

methyl 2-(3-oxo-2-pentylcyclopentyl)acetate
Chemical Formula: $C_{13}H_{22}O_3$
Molecular Weight: 226.31
Methyl Dihydro Jasmonate

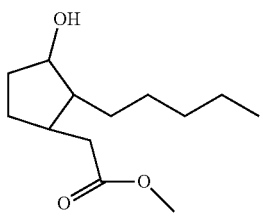

methyl 2-(3-hydroxy-2-pentylcyclopentyl)acetate
Chemical Formula: $C_{13}H_{24}O_3$
Molecular Weight: 228.33
Methyl Dihydro Jasmonate

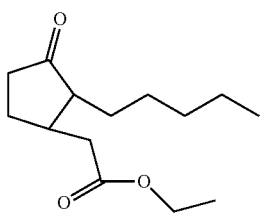

ethyl 2-(3-oxy-2-pentylcyclopentyl)acetate
Chemical Formula: $C_{14}H_{24}O_3$
Molecular Weight: 240.34
Ethyl Dihydro Jasmonate

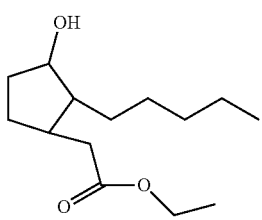

ethyl 2-(3-hydroxy-2-pentylcyclopentyl)acetate
Chemical Formula: $C_{14}H_{26}O_3$
Molecular Weight: 242.35
Ethyl Dihydro Jasmonate

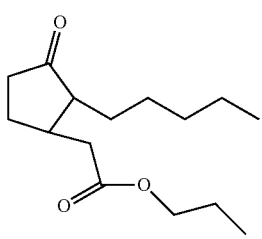

propyl 2-(3-oxo-2-pentylcyclopentyl)acetate
Chemical Formula: $C_{15}H_{26}O_3$
Molecular Weight: 254.37
Propyl Dihydro Jasmonate

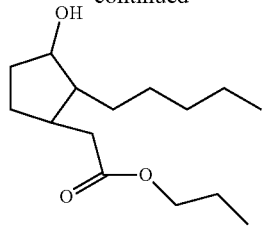

propyl 2-(3-hydroxy-2-pentylcyclopentyl)acetate
Chemical Formula: $C_{15}H_{28}O_3$
Molecular Weight: 256.38
Propyl Dihydro Jasmolate

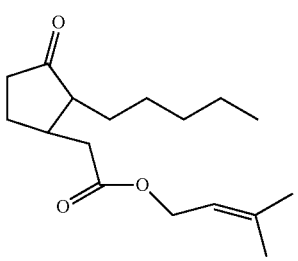

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate

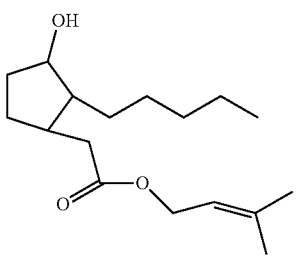

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate

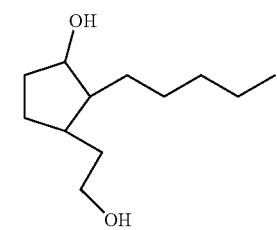

3-(2-hydroxyethyl)-2-pentylcyclopentanol
Chemical Formula: $C_{12}H_{24}O_2$
Molecular Weight: 200.32
MethylDihydroJasmodiol -continued

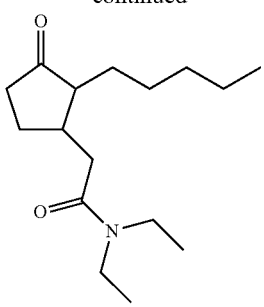

N,N-diethyl-2-(3-oxo-2-pentylcyclopentyl)acetamide
Chemical Formula: $C_{16}H_{29}NO_2$
Molecular Weight: 267.41
MDJ Amide

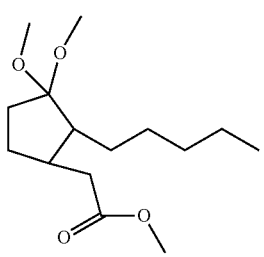

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

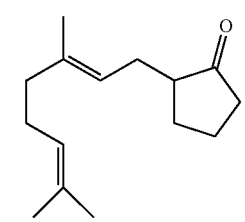

(E)-2-(3,7-dimethylocta-2,6-dienyl)cyclopentanone
Chemical Formula: $C_{15}H_{24}O$
Molecular Weight: 220.35
Apritone

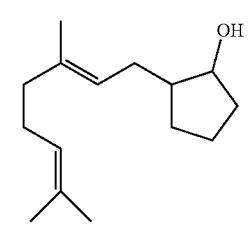

(E)-2-(3,7-dimethylocta-2,6-dienyl)cyclopentanol
Chemical Formula: $C_{15}H_{26}O$
Molecular Weight: 222.37
Apritol -continued

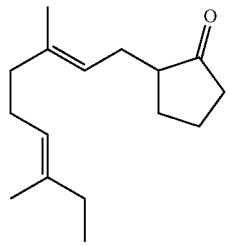

2-((2E,6E)-3,7-dimethylnona-2,6-dienyl)cyclopentanone
Chemical Formula: $C_{16}H_{26}O$
Molecular Weight: 234.38
Methyl Apritone

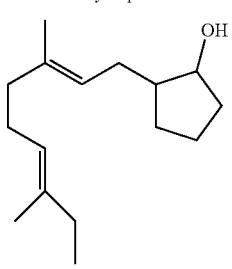

2-((2E,6E)-3,7-dimethylnona-2,6-dienyl)cyclopentanol
Chemical Formula: $C_{16}H_{28}O$
Molecular Weight: 236.39
Methyl Apritol

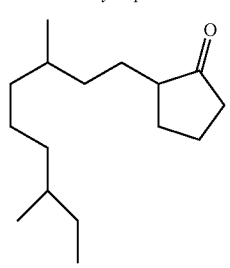

2-(3,7-dimethylnonyl)cyclopentanone
Chemical Formula: $C_{16}H_{30}O$
Molecular Weight: 238.41
Tetrahydromethyl Apritone

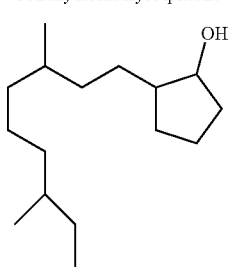

2-(3,7-dimethylnonyl)cyclopentanol
Chemical Formula: $C_{16}H_{32}O$
Molecular Weight: 240.42
Tetrahydromethyl Apritol

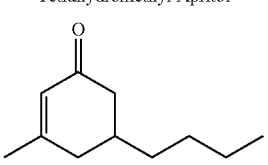

Chemical Formula: $C11H18O$
Molecular Weight: 166.26
3-methyl-5-butyl-2-cyclohexenone -continued

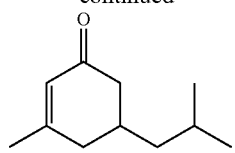

Chemical Formula: C11H18O
Molecular Weight: 166.26
3-methyl-5-isobutyl-2-cyclohexenone

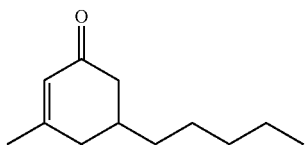

Chemical Formula: C12H20O
Molecular Weight: 180.29
3-methyl-5-pentyl-2-cyclohexenone

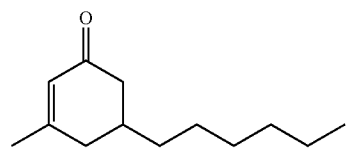

Chemical Formula: C13H22O
Molecular Weight: 194.31
3-methyl-5-hexyl-2-cyclohexenone

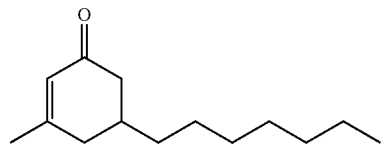

Chemical Formula: C14H24O
Molecular Weight: 208.34
3-methyl-5-heptyl-2-cyclohexenone

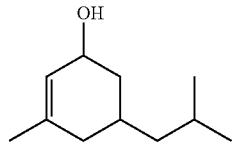

Chemical Formula: C11H20O
Molecular Weight: 168.28
3-methyl-5-isobutyl-2-cyclohexen-1-ol

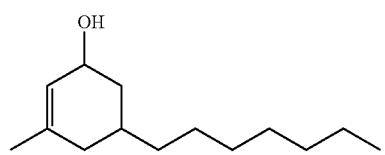

3-methyl-5-heptyl-2-cyclohexen-1-ol
Chemical Formula: C14H26O
Molecular Weight: 210.36

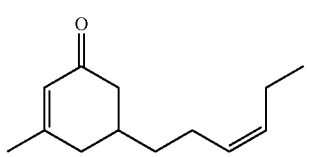

Chemical Formula: C13H20O
Molecular Weight: 192.30
3-methyl-5-(z-3-hexenyl)-2-cyclohexenone -continued

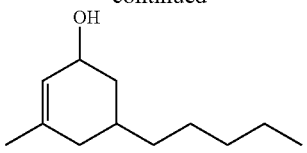

3-methyl-5-pentyl-2-cyclohexen-1-ol
Chemical Formula: C12H22O
Molecular Weight: 182.30

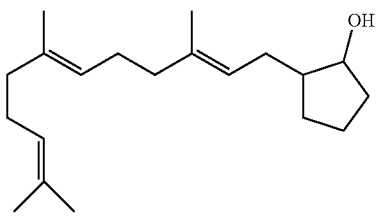

2-((2E,6E)-3,7,11-trimethyldodeca-2,6,10-trienyl)cyclopentanol
Chemical Formula: C20H34O
Molecular Weight: 290.48
Farnesylcyclopentanol

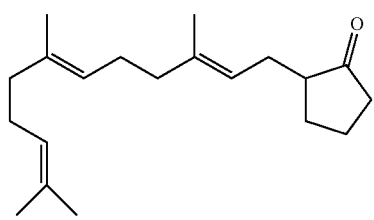

2-((2E,6E)-3,7,11-trimethyldodeca-2,6,10-trienyl)cyclopentanone
Chemical Formula: C20H32O
Molecular Weight: 288.47
Farnesylcyclopentanone

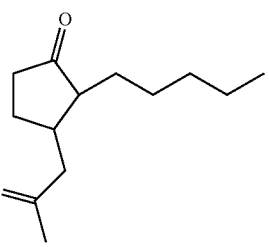

3-(2-oxopropyl)-2-pentylcyclopentanone
Chemical Formula: C13H22O2
Molecular Weight: 210.31
Amyl Cyclopentanone Propanone

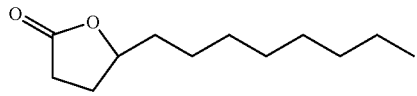

5-octyldihydrofuran-2(3H)-one
Chemical Formula: C12H22O2
Molecular Weight: 198.30
gamma-dodecalactone

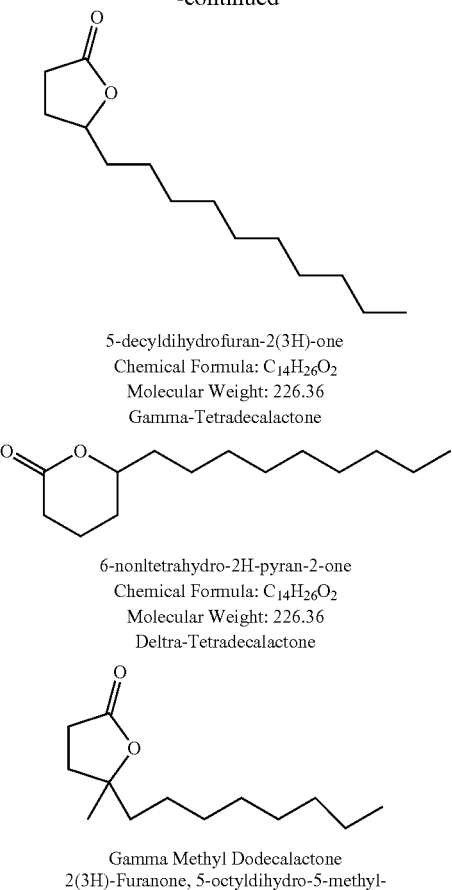

5-decyldihydrofuran-2(3H)-one
Chemical Formula: $C_{14}H_{26}O_2$
Molecular Weight: 226.36
Gamma-Tetradecalactone 6-nonltetrahydro-2H-pyran-2-one
Chemical Formula: $C_{14}H_{26}O_2$
Molecular Weight: 226.36
Deltra-Tetradecalactone Gamma Methyl Dodecalactone
2(3H)-Furanone, 5-octyldihydro-5-methyl-

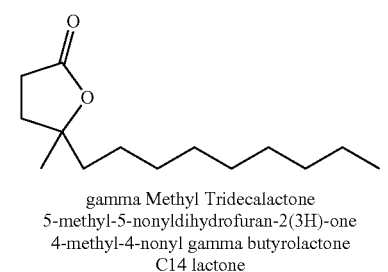

gamma Methyl Tridecalactone
5-methyl-5-nonyldihydrofuran-2(3H)-one
4-methyl-4-nonyl gamma butyrolactone
C14 lactone Chemical Formula: $C_{15}H_{28}O_2$
Molecular Weight: 240.38
Gamma Pentadecalactone

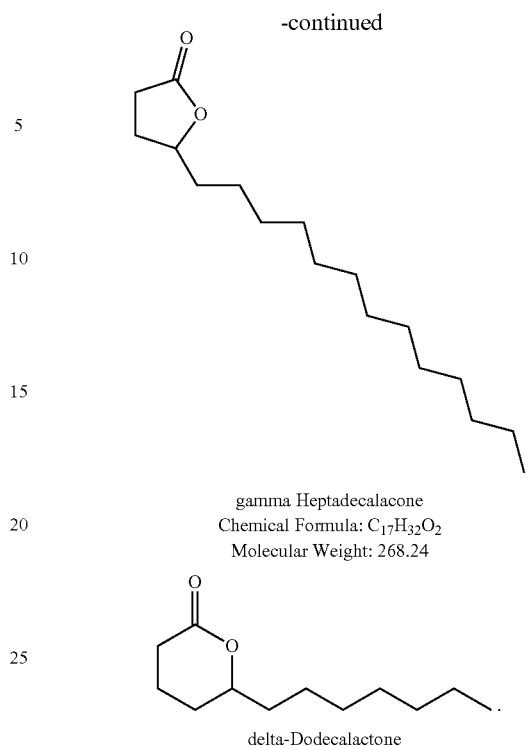

gamma Heptadecalacone
Chemical Formula: $C_{17}H_{32}O_2$
Molecular Weight: 268.24 delta-Dodecalactone

68. The synergistic biting arthropod repellent formulation of clause 62 wherein the compounds of structure (A) of compounds (a) comprise methyl apritone, methyl dihydrojasmonate, propyl dihydrojasmonate, gamma-dodecalactone, delta-dodecalactone, gamma-tridecalactone, gamma-tetradecalactone, gamma methyl dodecalactone, gamma methyl tridecalactone, 3-methyl-5-pentyl-2-cyclohexenone, 3-methyl-5-pentyl-2-cyclohexenol, 3-methyl-5-hexyl-2-cyclohexenone, and 3-methyl-5-heptyl-2-cyclohexenone.

69. The synergistic biting arthropod repellent formulation of clause 62 wherein the carboxylic acids of compounds (a) comprise lactic acid, salicylic acid, geranic acid, citronellic acid, 3-methyl-2-decenoic acid, and any isomers thereof.

70. The synergistic biting arthropod repellent formulation of clause 62 wherein the carboxylic acids of compounds (a) comprise lactic acid and isomers thereof.

71. The synergistic biting arthropod repellent formulation of clause 62 wherein the esters of carboxylic acids of compounds (a) comprise methyl lactate, ethyl lactate, propyl lactate, butyl lactate, amyl lactate, isoamyl lactate, hexyl lactate, cis-3-hexenyl lactate, methyl geranate, ethyl geranate, isoamyl geranate, methyl citronellate, ethyl citronellate, methyl salicylate, ethyl salicylate, amyl salicylate, isoamyl salicylate, hexyl salicylate, cis-3-hexenyl salicylate, and any isomers thereof.

72. The synergistic biting arthropod repellent formulation of clause 62 wherein the esters of carboxylic acids of compounds (a) comprise esters of salicylic acid and any isomers thereof.

73. The synergistic biting arthropod repellent formulation of clause 62 which comprises an alkoxy nootkatol, one or more of the compounds (a), and one or more of the repellents.

74. The synergistic biting arthropod repellent formulation of clause 62 which comprises an alkoxy nootkatol and two or more of the compounds (a), or an alkoxy nootkatol and two or more of the repellents.

75. The synergistic biting arthropod repellent formulation of clause 62 wherein the biting arthropods comprise ticks, mosquitoes and bed bugs.

76. The synergistic biting arthropod repellent formulation of clause 62 which is applied to the skin in the form of wipes, lotions, creams, oils, or sprays.

77. The synergistic biting arthropod repellent formulation of clause 62 which is applied to cleaning products.

78. The synergistic biting arthropod repellent formulation of clause 62 wherein the combined effect is greater repellency or protection time.

While we have shown and described several embodiments in accordance with our disclosure, it is to be clearly understood that the same may be susceptible to numerous changes apparent to one skilled in the art. Therefore, we do not wish to be limited to the details shown and described but intend to show all changes and modifications that come within the scope of the appended claims.

What is claimed is:

1. A method for the control or repellency of biting arthropods, the method comprising bringing the biting arthropods into contact with a biting arthropod repellent formulation, wherein the biting arthropod repellent formulation comprises an alkoxy nootkatol.

2. The method of claim 1 wherein the alkoxy nootkatol is methoxy nootkatol.

3. The method of claim 1 wherein the alkoxy nootkatol is present in an amount from about 0.5 weight percent to about 30 weight percent, based on the total weight of the biting arthropod repellent formulation.

4. The method of claim 1 wherein the biting arthropods comprise ticks, mosquitoes and bed bugs.

5. The method of claim 1 wherein the biting arthropod repellent formulation is applied to the skin in the form of wipes, lotions, creams, oils, or sprays, or is applied to cleaning products.

6. A method for the control or repellency of biting arthropods, the method comprising bringing the biting arthropods into contact with a biting arthropod repellent formulation, wherein the biting arthropod repellent formulation comprises:

(I) any combination of an alkoxy nootkatol in combination with one or more of compounds (a), wherein compounds (a) are selected from the group consisting of:

(1) alkyl ketones and cyclic ketones, saturated or unsaturated, branched or unbranched, containing from about 6 to about 18 carbon atoms, or any range of carbon atoms within said range;

(2) compounds of the structure (A)

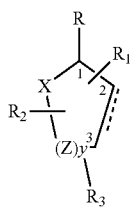

(A)

wherein:
R is selected from —OH, =O, —OC(O)R$_4$, —OR$_6$, and —(OR$_6$)$_2$, wherein each R$_6$ is independently selected from an alkyl group containing from about 1 to about 4 carbon atoms and R$_4$ is a branched or straight chain, saturated or unsaturated, hydrocarbyl group with zero to two double bonds and from about 1 to about 15 carbon atoms;

X is O or CH$_2$, with the proviso that when X is O, R, can only be =O;

each Z is independently selected from (CH) and (CH$_2$);

v is a numeral selected from 1 and 2;

R$_1$ is selected from H or a branched or straight chain, saturated or unsaturated, hydrocarbyl group with zero to two double bonds and from about 1 to about 15 carbon atoms;

R$_2$ is selected from H and a branched or straight chain, saturated or unsaturated, hydrocarbyl group with zero to three double bonds and from about 1 to about 15 carbon atoms;

R$_3$ is selected from H, a branched or straight chain, saturated or unsaturated, hydrocarbyl group with zero to three double bonds and from about 1 to about 15 carbon atoms, —(CH$_2$)$_n$OH, —C(O)OR$_5$, —CH$_2$C(O)OR$_7$, —CH$_2$C(O)R$_8$, —C(O)NR$_9$R$_{10}$, and —CH$_2$C(O)NR$_{11}$R$_{12}$, wherein each of R$_8$, R$_7$, R$_8$, R$_9$, R$_{10}$, R$_{11}$ and R$_{12}$ is independently selected from H and a branched or straight chain, saturated or unsaturated, hydrocarbyl group with zero to three double bonds and from about 1 to about 15 carbon atoms, and n is n integer of from 1 to 12;

the bond between the 2 and 3 positions in the ring structure may be a single or a double bond; and wherein the compounds of structure (A) contain from about 11 to about 20 carbon atoms except where R is =O, X=CH$_2$ and y is 1 the compounds of structure (A) contain from about 13 to about 20 carbon atoms, and includes optical isomers, diastereomers and enantiomers of the compounds of structure (A); and (3) branched or unbranched, straight chain or cyclic, saturated or unsaturated, carboxylic acids containing from about 3 to about 18 carbon atoms or any range of carbon atoms within said range, including isomers thereof; and (4) esters of branched or unbranched, straight chain or cyclic, saturated or unsaturated, carboxylic acids containing from about 3 to about 18 carbon atoms or any range of carbon atoms within said range, including isomers thereof; or (II) any combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds.

7. The method of claim 6 wherein the alkoxy nootkatol is methoxy nootkatol.

8. The method of claim 6 wherein the alkoxy nootkatol is present in an amount from about 0.5 weight percent to about 30 weight percent, and the one or more compounds (a), or the one or more repellents, are present in an amount from about 0.5 weight percent to about 25 weight percent, based on the total weight of the biting arthropod repellent formulation.

9. The method of claim 6 wherein the alkyl and cyclic ketones of compound (a) comprise geranyl acetone (6,10-dimethyl-5,9-undecadien-2-one), farnesyl acetone (5,9,13-pentadecatrien-2-one), 6,10,14-trimethyl-)methyl undecyl ketone (2-tridecanone), methyl decyl ketone (2-dodecanone), alpha-ionone (4-(2,6,6-trimethyl-2-cyclohexenyl)-3-buten-2-one), beta ionone (4-(2,6,6-trimethyl-1-cyclohexenyl)-3-buten-2-one), alpha-isomethylionone (3-methyl-4-(2,6,6-trimethyl-2-cyclohexen-1-yl)-3-buten-2-one), isobutylionone ((E)-5-methyl-1-(2,6,6-trimethyl-1-cyclohex-2-enyl) hex-1-en-3-one), isolongifolen-9-one ((1R)-2,2,7,7-tetramethyltricyclo[6.2.1.01,6]undec-5-en-4-one), dimethylionone ((E)-2-methyl-1-(2,2,6-trimethyl-1-cyclohex-3-enyl)pent-1-en-3-one), isolongifolanone (2,2,7,7-tetramethyltricyclo[6.2.1.01,6]undecan-5-one), pseudoionone (6,10-dimethyl-3,5,9-undecatrien-2-one), 2-cyclopentylcyclopentanone, methyl nonyl ketone (2-undecanone), and 3-decen-2-one.

10. The method of claim 6 wherein the alkyl and cyclic ketones of compound (a) comprise methyl decyl ketone, methyl undecyl ketone, methyl nonyl ketone, geranyl acetone, farnesyl acetone, ionone, and isolongifolenone.

11. The method of claim 6 wherein the compounds of structure (A) of compound (a) comprise compounds having the formula

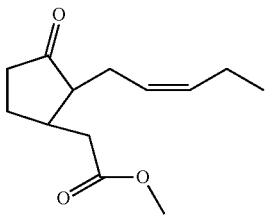

(Z)-methyl 2-(3-oxo-2-(pent-2-enyl)cyclopentyl)acetate
Chemical Formula: $C_{13}H_{20}O_3$
Molecular Weight: 224.30
Methyl Jasmonate

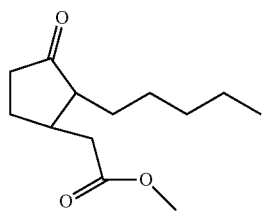

methyl 2-(3-oxo-2-pentylcyclopentyl)acetate
Chemical Formula: $C_{13}H_{22}O_3$
Molecular Weight: 226.31
Methyl Dihydro Jasmonate

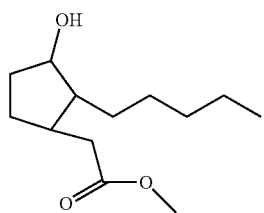

methyl 2-(3-hydroxy-2-pentylcyclopentyl)acetate
Chemical Formula: $C_{13}H_{24}O_3$
Molecular Weight: 228.33
Methyl Dihydro Jasmolate -continued

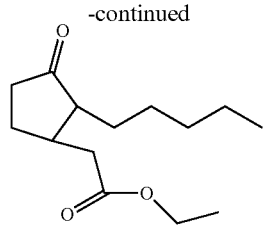

ethyl 2-(3-oxy-2-pentylcyclopentyl)acetate
Chemical Formula: $C_{14}H_{24}O_3$
Molecular Weight: 240.34
Ethyl Dihydro Jasmonate

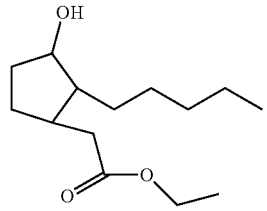

ethyl 2-(3-hydroxy-2-pentylcyclopentyl)acetate
Chemical Formula: $C_{14}H_{26}O_3$
Molecular Weight: 242.35
Ethyl Dihydro Jasmolate

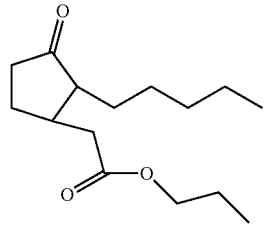

propyl 2-(3-oxo-2-pentylcyclopentyl)acetate
Chemical Formula: $C_{15}H_{26}O_3$
Molecular Weight: 254.37
Propyl Dihydro Jasmonate

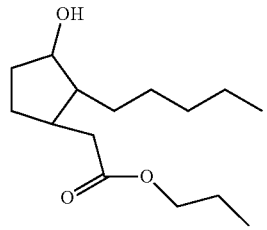

propyl 2-(3-hydroxy-2-pentylcyclopentyl)acetate
Chemical Formula: $C_{15}H_{28}O_3$
Molecular Weight: 256.38
Propyl Dihydro Jasmolate

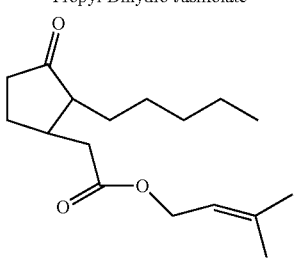

3-methylbut-2-enyl 2-(3-oxo-2-pentylcyclopentyl)acetate
Chemical Formula: $C_{17}H_{28}O_3$
Molecular Weight: 280.40
Prenyl Dihydro Jasmonate

67

-continued

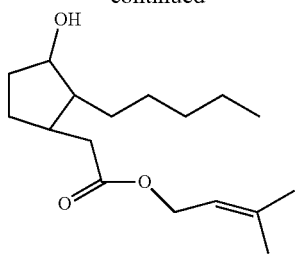

3-methylbut-2-enyl 2-(3-hydroxy-2-pentylcyclopentyl)acetate
Chemical Formula: $C_{17}H_{30}O_3$
Molecular Weight: 282.42
Prenyl Dihydro Jasmolate

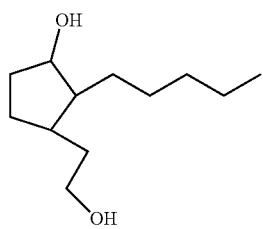

3-(2-hydroxyethyl)-2-pentylcyclopentanol
Chemical Formula: $C_{12}H_{24}O_2$
Molecular Weight: 200.32
MethylDihydroJasmodiol

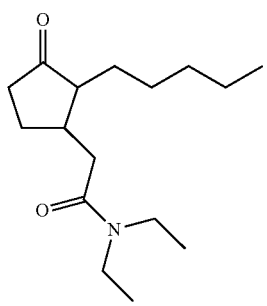

N,N-diethyl-2-(3-oxo-2-pentylcyclopentyl)acetamide
Chemical Formula: $C_{16}H_{29}NO_2$
Molecular Weight: 267.41
MDJ Amide

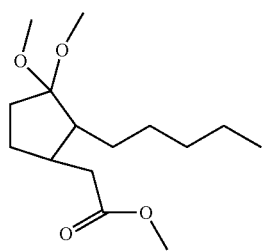

methyl 2-(3,3-dimethoxy-2-pentylcyclopentyl)acetate
Chemical Formula: $C_{15}H_{28}O_4$
Molecular Weight: 272.38
Methyl Dihydro Jasmonate Dimethyl Ketal

68

-continued

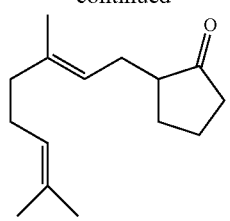

(E)-2-(3,7-dimethylocta-2,6-dienyl)cyclopentanone
Chemical Formula: $C_{15}H_{24}O$
Molecular Weight: 220.35
Apritone

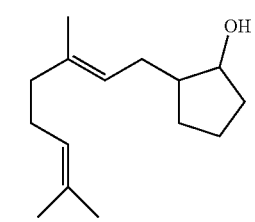

(E)-2-(3,7-dimethylocta-2,6-dienyl)cyclopentanol
Chemical Formula: $C_{15}H_{26}O$
Molecular Weight: 222.37
Apritol

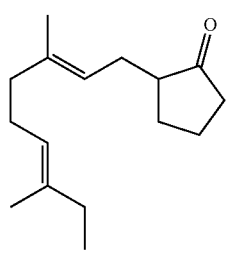

2-((2E,6E)-3,7-dimethylnona-2,6-dienyl)cyclopentanone
Chemical Formula: $C_{16}H_{26}O$
Molecular Weight: 234.38
Methyl Apritone

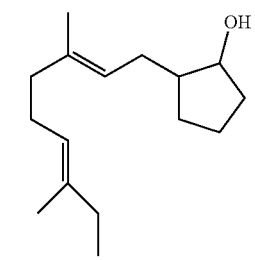

2-((2E,6E)-3,7-dimethylnona-2,6-dienyl)cyclopentanol
Chemical Formula: $C_{16}H_{28}O$
Molecular Weight: 236.39
Methyl Apritol -continued

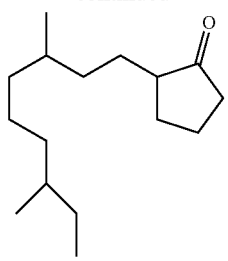

2-(3,7-dimethylnonyl)cyclopentanone
Chemical Formula: C$_{16}$H$_{30}$O
Molecular Weight: 238.41
Tetrahydromethyl Apritone

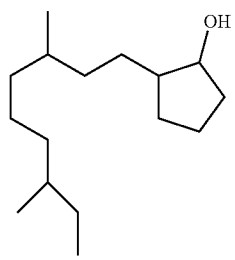

2-(3,7-dimethylnonyl)cyclopentanol
Chemical Formula: C$_{16}$H$_{32}$O
Molecular Weight: 240.42
Tetrahydromethyl Apritol

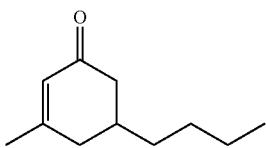

Chemical Formula: C11H18O
Molecular Weight: 166.26
3-methyl-5-butyl-2-cyclohexenone

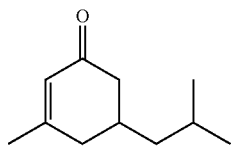

Chemical Formula: C11H18O
Molecular Weight: 166.26
3-methyl-5-isobutyl-2-cyclohexenone

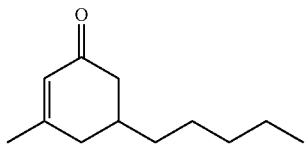

Chemical Formula: C12H20O
Molecular Weight: 180.29
3-methyl-5-pentyl-2-cyclohexenone

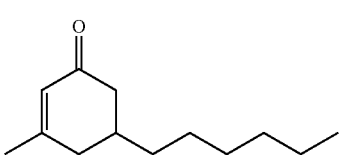

Chemical Formula: C13H22O
Molecular Weight: 194.31
3-methyl-5-hexyl-2-cyclohexenone -continued

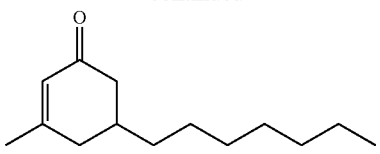

Chemical Formula: C14H24O
Molecular Weight: 208.34
3-methyl-5-heptyl-2-cyclohexenone

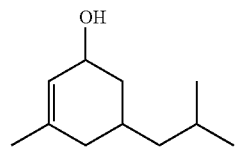

Chemical Formula: C11H20O
Molecular Weight: 168.28
3-methyl-5-isobutyl-2-cyclohexen-1-ol

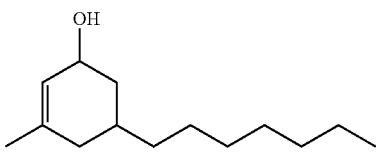

3-methyl-5-heptyl-2-cyclohexen-1-ol
Chemical Formula: C14H26O
Molecular Weight: 210.36

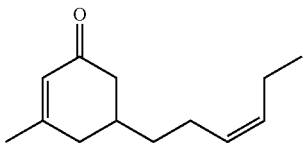

Chemical Formula: C13H20O
Molecular Weight: 192.30
3-methyl-5-(z-3-hexenyl)-2-cyclohexenone

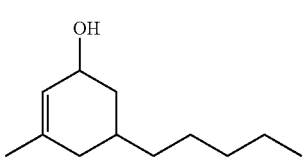

3-methyl-5-pentyl-2-cyclohexen-1-ol
Chemical Formula: C12H22O
Molecular Weight: 182.30

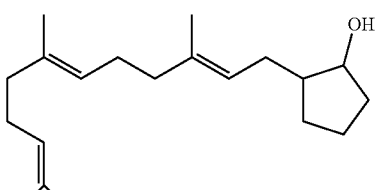

2-((2E,6E)-3,7,11-trimethyldodeca-2,6,10-trienyl)cyclopentanol
Chemical Formula: C$_{20}$H$_{34}$O
Molecular Weight: 290.48
Farnesylcyclopentanol -continued

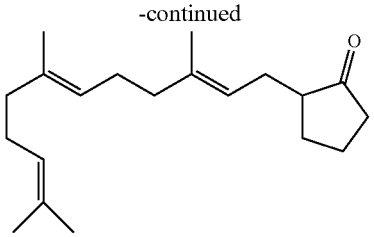

2-((2E,6E)-3,7,11-trimethyldodeca-2,6,10-trienyl)cyclopentanone
Chemical Formula: $C_{20}H_{32}O$
Molecular Weight: 288.47
Farnesylcyclopentanone

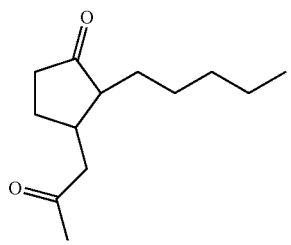

3-(2-oxopropyl)-2-pentylcyclopentanone
Chemical Formula: $C_{13}H_{22}O_2$
Molecular Weight: 210.31
Amyl Cyclopentanone Propanone

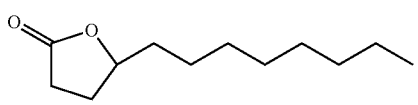

5-octyldihydrofuran-2(3H)-one
Chemical Formula: $C_{12}H_{22}O_2$
Molecular Weight: 198.30
gamma-dodecalactone

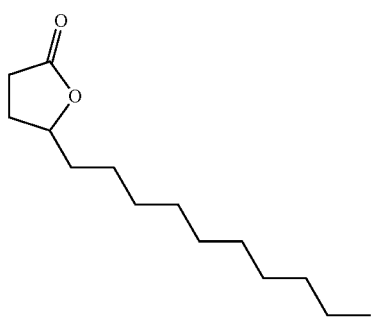

5-decyldihydrofuran-2(3H)-one
Chemical Formula: $C_{14}H_{26}O_2$
Molecular Weight: 226.36
Gamma-Tetradecalactone

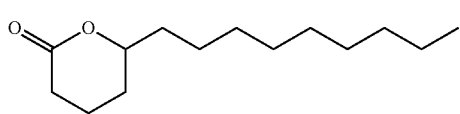

6-nonltetrahydro-2H-pyran-2-one
Chemical Formula: $C_{14}H_{26}O_2$
Molecular Weight: 226.36
Deltra-Tetradecalactone -continued

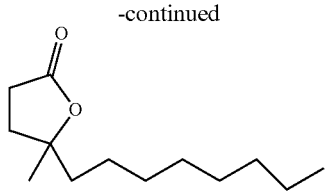

Gamma Methyl Dodecalactone
2(3H)-Furanone, 5-octyldihydro-5-methyl-

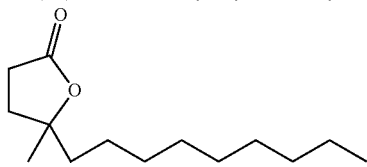

gamma Methyl Tridecalactone
5-methyl-5-nonyldihydrofuran-2(3H)-one
4-methyl-4-nonyl gamma butyrolactone
C14 lactone

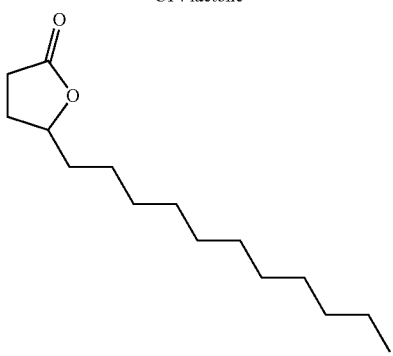

Chemical Formula: $C_{15}H_{28}O_2$
Molecular Weight: 240.38
Gamma Pentadecalactone

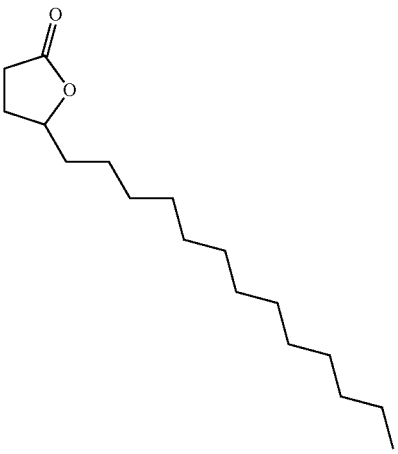

gamma Heptadecalacone
Chemical Formula: $C_{17}H_{32}O_2$
Molecular Weight: 268.24

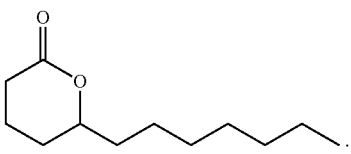

delta-Dodecalactone

12. The method of claim 6 wherein the compounds of structure (A) of compounds (a) comprise methyl apritone, methyl dihydrojasmonate, propyl dihydrojasmonate, gamma-dodecalactone, delta-dodecalactone, gamma-tridecalactone, gamma-tetradecalactone, gamma methyl dodecalactone, gamma methyl tridecalactone, 3-methyl-5-pentyl-2-cyclohexenone, 3-methyl-5-pentyl-2-cyclohexenol, 3-methyl-5-hexyl-2-cyclohexenone, and 3-methyl-5-heptyl-2-cyclohexenone.

13. The method of claim 6 wherein the carboxylic acids of compounds (a) comprise lactic acid, salicylic acid, geranic acid, citronellic acid, 3-methyl-2-decenoic acid, and any isomers thereof.

14. The method of claim 6 wherein the carboxylic acids of compounds (a) comprise lactic acid and isomers thereof.

15. The method of claim 6 wherein the esters of carboxylic acids of compounds (a) comprise methyl lactate, ethyl lactate, propyl lactate, butyl lactate, amyl lactate, isoamyl lactate, hexyl lactate, cis-3-hexenyl lactate, methyl geranate, ethyl geranate, isoamyl geranate, methyl citronellate, ethyl citronellate, methyl salicylate, ethyl salicylate, amyl salicylate, isoamyl salicylate, hexyl salicylate, cis-3-hexenyl salicylate, and any isomers thereof.

16. The method of claim 6 wherein the esters of carboxylic acids of compounds (a) comprise esters of salicylic acid and any isomers thereof.

17. The method of claim 6 wherein the biting arthropod repellent formulation comprises an alkoxy nootkatol, one or more of the compounds (a), and one or more of the repellents.

18. The method of claim 6 wherein the biting arthropod repellent formulation comprises an alkoxy nootkatol and two or more of the compounds (a), or an alkoxy nootkatol and two or more of the repellents.

19. The method of claim 6 wherein the biting arthropods comprise ticks, mosquitoes and bed bugs.

20. A method for the control or repellency of biting arthropods, the method comprising bringing the biting arthropods into contact with a synergistic biting arthropod repellent formulation, wherein the synergistic biting arthropod repellent formulation comprises:
(I) any synergistic combination of an alkoxy nootkatol in combination with one or more of compounds (a), wherein compounds (a) are selected from the group consisting of:
(1) alkyl ketones and cyclic ketones, saturated or unsaturated, branched or unbranched, containing from about 6 to about 18 carbon atoms, or any range of carbon atoms within said range;
(2) compounds of the structure (A)

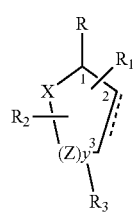

(A)

wherein:
R is selected from —OH, =O, —OC(O)$R_4$, —O$R_6$, and —(O$R_6$)$_2$, wherein each $R_6$ is independently selected from an alkyl group containing from about 1 to about 4 carbon atoms and $R_4$ is a branched or straight chain, saturated or unsaturated hydrocarbyl group with zero to two double bonds and from about 1 to about 15 carbon atoms;
X is O or $CH_2$, with the proviso that when X is O, R, can only be =O;
each Z is independently selected from (CH) and ($CH_2$);
y is a numeral selected from 1 and 2;
$R_1$ is selected from H or a branched or straight chain, saturated or unsaturated, hydrocarbyl group with zero to two double bonds and from about 1 to about 15 carbon atoms;
$R_2$ is selected from H and a branched or straight chain, saturated or unsaturated, hydrocarbyl group with zero to three double bonds and from about 1 to about 15 carbon atoms;
$R_3$ is selected from H, a branched or straight chain, saturated or unsaturated, hydrocarbyl group with zero to three double bonds and from about 1 to about 15 carbon atoms, —($CH_2$)$_n$OH, —C(O)O$R_5$, —$CH_2$C(O)O$R_7$, —$CH_2$C(O)$R_8$, —C(O)N$R_9R_{10}$, and —$CH_2$C(O)N$R_{11}R_{12}$, wherein each of $R_5$, $R_7$, $R_8$, $R_9$, $R_{10}$, $R_{11}$ and $R_{12}$ is independently selected from H and a branched or straight chain, saturated or unsaturated, hydrocarbyl group with zero to three double bonds and from about 1 to about 15 carbon atoms, and n is n integer of from 1 to 12;
the bond between the 2 and 3 positions in the ring structure may be a single or a double bond; and
wherein the compounds of structure (A) contain from about 11 to about 20 carbon atoms except where R is =O, X=$CH_2$ and y is 1 the compounds of structure (A) contain from about 13 to about 20 carbon atoms, and includes optical isomers, diastereomers and enantiomers of the compounds of structure (A); and
(3) branched or unbranched, straight chain or cyclic, saturated or unsaturated, carboxylic acids containing from about 3 to about 18 carbon atoms or any range of carbon atoms within said range, including isomers thereof; and
(4) esters of branched or unbranched, straight chain or cyclic, saturated or unsaturated, carboxylic acids containing from about 3 to about 18 carbon atoms or any range of carbon atoms within said range, including isomers thereof; or
(II) any synergistic combination of an alkoxy nootkatol in combination with one or more repellents selected from the group consisting of N,N-Diethyl-3-methylbenzamide, para-menthane-3,8-diol (PMD), Picaridin, ethyl 3-[acetyl(butyl)amino]propanoate (IR3535), and other nitrogen-containing repellents including amines, amides, and nitrogen-containing heterocyclic compounds;
wherein the synergistic combination of the alkoxy nootkatol in combination with the one or more of compounds (a) and/or the synergistic combination of the alkoxy nootkatol in combination with the one or more repellents, produces a combined effect greater than the sum of their separate effects.

* * * * *